(12) United States Patent
Shannon et al.

(10) Patent No.: US 9,018,267 B2
(45) Date of Patent: Apr. 28, 2015

(54) SOLID SUPPORT WITH A GRAFTED CHAIN

(71) Applicant: 3M Innovative Properties Company, St. Paul, MN (US)

(72) Inventors: Simon K. Shannon, Woodbury, MN (US); Catherine A. Bothof, Stillwater, MN (US); Babu N. Gaddam, Woodbury, MN (US); Jerald K. Rasmussen, Woodville, WI (US); Richard B. Ross, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/254,247

(22) Filed: Apr. 16, 2014

(65) Prior Publication Data
US 2014/0228457 A1 Aug. 14, 2014

Related U.S. Application Data

(62) Division of application No. 14/058,561, filed on Oct. 21, 2013, now Pat. No. 8,735,455, which is a division of application No. 13/000,435, filed as application No. PCT/US2009/043455 on May 11, 2009, now Pat. No. 8,592,493.

(60) Provisional application No. 61/075,934, filed on Jun. 26, 2008.

(51) Int. Cl.

| | | |
|---|---|---|
| *B01D 15/08* | (2006.01) | |
| *B01J 39/18* | (2006.01) | |
| *C08F 20/56* | (2006.01) | |
| *C08F 271/02* | (2006.01) | |
| *B01J 20/286* | (2006.01) | |
| *B01J 20/32* | (2006.01) | |
| *B01J 39/16* | (2006.01) | |
| *B01J 41/12* | (2006.01) | |
| *B01J 20/26* | (2006.01) | |
| *B01J 20/287* | (2006.01) | |
| *C07K 1/22* | (2006.01) | |
| *B01J 39/20* | (2006.01) | |
| *B01J 41/14* | (2006.01) | |
| *B01D 15/38* | (2006.01) | |

(52) U.S. Cl.
CPC .............. *C08F 271/02* (2013.01); *B01D 15/08* (2013.01); *B01D 15/3804* (2013.01); *B01J 20/286* (2013.01); *B01J 20/3242* (2013.01); *B01J 20/3278* (2013.01); *B01J 20/328* (2013.01); *B01J 39/165* (2013.01); *B01J 39/18* (2013.01); *B01J 41/12* (2013.01); *B01J 20/264* (2013.01); *B01J 20/287* (2013.01); *B01J 20/3204* (2013.01); *B01J 20/3208* (2013.01); *B01J 20/3219* (2013.01); *B01J 20/3255* (2013.01); *B01J 20/3276* (2013.01); *B01J 2220/54* (2013.01); *B01J 2220/62* (2013.01); *B01J 2220/58* (2013.01); *C07K 1/22* (2013.01); *B01J 39/20* (2013.01); *B01J 41/14* (2013.01)

(58) Field of Classification Search
CPC .... B01D 15/08; B01J 20/286; B01J 20/3242; B01J 39/18; B01J 49/00; C08F 271/02; C08F 20/56; C08F 8/32; C08F 220/56; C08F 8/14
USPC ............ 521/33, 32; 524/556; 525/329.4, 384, 525/380, 379
See application file for complete search history.

(56) References Cited

U.S. PATENT DOCUMENTS

| | | | |
|---|---|---|---|
| 4,153,661 A | 5/1979 | Ree | |
| 4,157,418 A | 6/1979 | Heilmann | |
| 4,378,411 A | 3/1983 | Heilmann | |
| 4,387,411 A * | 6/1983 | Clausen et al. | ............... 360/128 |
| 4,539,256 A | 9/1985 | Shipman | |
| 4,565,663 A | 1/1986 | Errede | |
| 4,737,560 A | 4/1988 | Heilmann | |
| 4,810,381 A | 3/1989 | Hagen | |
| 4,871,824 A | 10/1989 | Heilmann | |
| 4,946,753 A | 8/1990 | Elmasry | |

(Continued)

FOREIGN PATENT DOCUMENTS

| | | |
|---|---|---|
| CA | 1330074 | 6/1994 |
| EP | 0337144 | 10/1989 |

(Continued)

OTHER PUBLICATIONS

S. Heilmann et al: "Chemistry of Alkenyl Azlactones. I. Radiation-Sensitive Materials Derived From Azlactone-Containing Copolymers", Journal of Polymer Science, vol. 22, No. 5, 1984, pp. 1179-1186.*

(Continued)

*Primary Examiner* — Michael M Bernshteyn
(74) *Attorney, Agent, or Firm* — Jean A. Lown

(57) ABSTRACT

Articles that contain a solid support with a grafted chain extending from the solid support, methods of making these articles, and various uses of the articles are described. More specifically, the grafted chain has a functional group that can react with or interact with target compound. Alternatively, the functional group on the grafted chain can react with a modifying agent to provide another group that can react with or interact with the target compound. The grafted chains are attached to the solid support through a ring-opened azlactone group. The articles can be used to purify the target compound or to separate the target compound from other molecules in a sample.

9 Claims, No Drawings

(56) References Cited

U.S. PATENT DOCUMENTS

| | | |
|---|---|---|
| 4,957,943 A | 9/1990 | McAllister |
| 4,971,736 A | 11/1990 | Hagen |
| 5,075,352 A | 12/1991 | Elmasry |
| 5,278,023 A | 1/1994 | Bills |
| 5,292,514 A | 3/1994 | Capecchi |
| 5,292,840 A | 3/1994 | Heilmann |
| 5,336,742 A | 8/1994 | Heilmann |
| 5,344,701 A | 9/1994 | Gagnon |
| 5,403,902 A | 4/1995 | Heilmann |
| 5,408,002 A | 4/1995 | Coleman |
| 5,476,665 A | 12/1995 | Dennison |
| 5,503,933 A | 4/1996 | Afeyan |
| 5,510,421 A | 4/1996 | Dennison |
| 5,561,097 A | 10/1996 | Gleason |
| 5,647,987 A | 7/1997 | Müller |
| 5,667,692 A | 9/1997 | Müller |
| 5,750,245 A | 5/1998 | Exsted |
| 5,993,935 A | 11/1999 | Rasmussen |
| 6,063,484 A | 5/2000 | Exsted |
| 6,149,994 A | 11/2000 | Mueller |
| 6,156,478 A | 12/2000 | Liu |
| 6,291,216 B1 | 9/2001 | Muller |
| 6,379,952 B1 | 4/2002 | Rasmussen |
| 6,428,707 B1 | 8/2002 | Berg |
| 6,448,301 B1 | 9/2002 | Gaddam |
| 6,548,607 B2 | 4/2003 | Halverson |
| 6,635,690 B2 | 10/2003 | Heilmann |
| 6,787,635 B2 | 9/2004 | Rasmussen |
| 6,794,458 B2 | 9/2004 | Haddad |
| 7,060,187 B2 | 6/2006 | Ihre |
| 7,166,696 B2 | 1/2007 | Rasmussen |
| 8,569,072 B2 | 10/2013 | Halverson |
| 8,592,493 B2 | 11/2013 | Shannon |
| 2014/0046029 A1 | 2/2014 | Shannon |

FOREIGN PATENT DOCUMENTS

| | | |
|---|---|---|
| EP | 0565978 | 10/1993 |
| JP | 2002-294308 | 10/2002 |
| WO | WO 93/25594 | 12/1993 |
| WO | WO 95/09695 | 4/1995 |
| WO | WO 97/49754 | 12/1997 |

OTHER PUBLICATIONS

Heilmann, "Chemistry of Alkenyl Azlactones. I. Radiation-Sensitive Materials Derived from Azlactone-Containing Copolymers", Journal of Polymer Science: Polymer Chemistry Edition, May 1984, vol. 22, Issue 5, pp. 1179-1186. (XP-002578784).

Horak, "Poly(ethylene dimethacrylate) particles with poly(glycidyl methacrylate) functionalities", Polymer, Mar. 1994, vol. 35, Issue 6, pp. 1195-1202.

Johnson, "Reproducibility of physical characteristics, protein immobilization and chromatographic performance of 3M Emphaze Biosupport Medium AB 1", Journal of Chromatography A, Apr. 29, 1994, vol. 667, Issues 1-2, pp. 1-9.

Rasmussen, "Mechanistic Studies on the Reverse Phase Suspension Copolymerization of Vinyldimethylazlactone and Methylenebisacrylamide", Makromol. Chem., Macromol. Symp., 54/55, pp. 535-550, (1992).

Unsal, "Monodisperse porous polymer particles with polyionic ligands for ion exchange separation of proteins", Analytica Chimica Acta, Jun. 16, 2006, vol. 570, Issue 2, pp. 240-248.

International Search Report for PCT/US2009/043455, 4 pages.

\* cited by examiner

SOLID SUPPORT WITH A GRAFTED CHAIN

CROSS REFERENCE TO RELATED APPLICATION

This application is a divisional application of pending prior U.S. application Ser. No. 14/058,561, filed Oct. 21, 2013, now allowed, which is a divisional application of U.S. Application of 13/000,435, filed Dec. 21, 2010, now granted U.S. Pat. No. 8,592,493, which is a national stage filing under 35 U.S.C. §371 of International Application No. PCT/US2009/043455, filed May 11, 2009, which claims the benefit of U.S. Provisional Patent Application No. 61/075,934, filed Jun. 26, 2008, the disclosures of which are incorporated by reference herein in their entireties.

TECHNICAL FIELD

Articles that include a solid support and a grafted chain with a functional group extending from the solid support, methods of making these articles, and various uses of these articles are described.

BACKGROUND

Various solid supports have been used for the separation and/or purification of target compounds. For example, various polymeric solid supports have been used to purify or separate target compounds based on the presence of an ionic group, based on the size of the target compound, based on a hydrophobic interaction, based on an affinity interaction, or based on the formation of a covalent bond.

In the biotechnology industry, large-scale separation and/or purification of various biomolecules such as proteins, enzymes, vaccines, DNA, RNA, and the like are of great interest. Improved materials and methods for separating and purifying biomolecules are desired.

SUMMARY

Articles that contain a solid support with a grafted chain extending from the solid support, methods of making these articles, and various uses of the articles are described. More specifically, the grafted chain has a functional group that can react with or interact with a target compound. Alternatively, the functional group on the grafted chain can react with a modifying agent to provide another group that can react with or interact with the target compound. The grafted chains are attached to the solid support through a ring-opened azlactone group.

In a first aspect, a method of preparing an article is provided. The article includes a solid support and a grafted chain extending from the solid support. The method of preparing the article includes providing an azlactone-functionalized support of Formula (I).

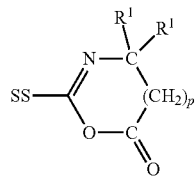
(I)

In Formula (I), SS refers to a solid support, the variable p is an integer equal to 0 or 1, and each $R^1$ is independently selected from alkyl, heteroalkyl, aryl, or aralkyl. The method further includes forming a (meth)acryloyl-functionalized support of Formula (II)

$$SS\text{-}(CO)\text{---}NH\text{---}C(R^1)_2\text{---}(CH_2)_p\text{---}(CO)\text{-}Q\text{-}Y^1\text{-}Q\text{-}(CO)\text{---}CR^2\text{=}CH_2 \quad (II)$$

from the azlactone-functionalized support of Formula (I). In Formula (II), each Q is independently a divalent group selected from oxy, thio, or $-NR^3-$ where $R^3$ is a hydrogen, alkyl, heteroalkyl, aryl, or aralkyl. Group $Y^1$ is a first linking group that contains an alkylene, heteroalkylene, arylene, or combination thereof. The group $R^2$ is hydrogen or an alkyl. The method still further includes reacting the (meth)acryloyl-functional support of Formula (II) with a monomer composition that contains a monomer of Formula (III)

$$Z^1\text{---}Y^2\text{---}CR^2\text{=}CH_2 \quad (III)$$

to form a grafted support of Formula (IV).

$$SS\text{-}(CO)\text{---}NH\text{---}C(R^1)_2\text{---}(CH_2)_p\text{---}(CO)\text{-}Q\text{-}Y^1\text{-}Q\text{-}(CO)\text{---}CR^2U^2\text{---}CH_2\text{---}U^1 \quad (IV)$$

The group $U^1$ includes at least one divalent monomeric unit of formula $-CR^2(Y^2Z^1)-CH_2-$. Group $U^2$ is selected from hydrogen or a group that includes at least one divalent monomeric unit of formula $-CR^2(Y^2Z^1)-CH_2-$. The group $Y^2$ is a second linking group selected from a single bond or a divalent group that contains an alkylene, heteroalkylene, arylene, or combination thereof. Group $Z^1$ is a functional group selected from (1) an acidic group or a salt thereof, (2) an amino group or a salt thereof, (3) a hydroxyl group, (4) an azlactone group or a precursor of the azlactone group, (5) a glycidyl group, or (6) a combination thereof.

In a second aspect, an article is provided that includes a grafted support of Formula (IV).

$$SS\text{-}(CO)\text{---}NH\text{---}C(R^1)_2\text{---}(CH_2)_p\text{---}(CO)\text{-}Q\text{-}Y^1\text{-}Q\text{-}(CO)\text{---}CR^2U^2\text{---}CH_2\text{---}U^1 \quad (IV)$$

In Formula (IV), SS is a solid support and $R^1$ is each independently selected from alkyl, heteroalkyl, aryl, or aralkyl. The variable p is an integer equal to 0 or 1. Each group Q is independently a divalent group selected from oxy, thio, or $-NR^3-$ where $R^3$ is hydrogen, alkyl, heteroalkyl, aryl, or aralkyl. Group $Y^1$ is a first linking group that contains an alkylene, heteroalkylene, arylene, or combination thereof. The group $R^2$ is hydrogen or an alkyl. The group $U^1$ includes at least one divalent monomeric unit of formula $-CR^2(Y^2Z^1)-CH_2-$. Group $U^2$ is selected from hydrogen or a group that includes at least one divalent monomeric unit of formula $-CR^2(Y^2Z^1)-CH_2-$. The group $Y^2$ is a second linking group selected from a single bond or a divalent group that contains an alkylene, heteroalkylene, arylene, or combination thereof. Group $Z^1$ is a functional group selected from (1) an acidic group or a salt thereof, (2) an amino group or a salt thereof, (3) a hydroxyl group, (4) an azlactone group or a precursor of the azlactone group, (5) a glycidyl group, or (6) a combination thereof.

In a third aspect, a (meth)acryloyl-functionalized support of Formula (II) is provided.

$$SS\text{-}(CO)\text{---}NH\text{---}C(R^1)_2\text{---}(CH_2)_p\text{---}(CO)\text{-}Q\text{-}Y^1\text{-}Q\text{-}(CO)\text{---}CR^2\text{=}CH_2 \quad (II)$$

In Formula (II), SS is a solid support and $R^1$ is each independently selected from alkyl, heteroalkyl, aryl, or aralkyl. The variable p is an integer equal to 0 or 1. Each Q is independently a divalent group selected from oxy, thio, or $-NR^3-$ where $R^3$ is hydrogen, alkyl, heteroalkyl, aryl, or aralkyl. Group $Y^1$ is a first linking group that contains an alkylene, heteroalkylene, arylene, or combination thereof. The group $R^2$ is hydrogen or an alkyl.

In a fourth aspect, a method of preparing an article is provided. The article includes a solid support and a grafted chain extending form the solid support. The method includes providing an azlactone-functionalized support of Formula (I).

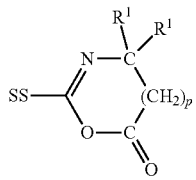

(I)

In Formula (I), SS refers to a solid support, the variable p is an integer equal to 0 or 1, and each $R^1$ is independently selected from alkyl, heteroalkyl, aryl, or aralkyl. The method further includes forming a (meth)acryloyl-functionalized support of Formula (II)

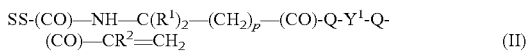

(II)

from the azlactone-functionalized support of Formula (I). In Formula (II), each Q is independently a divalent group selected from oxy, thio, or —$NR^3$— where $R^3$ is a hydrogen, alkyl, heteroalkyl, aryl, or aralkyl. Group $Y^1$ is a first linking group that contains an alkylene, heteroalkylene, arylene, or combination thereof. The group $R^2$ is hydrogen or an alkyl. The method still further includes reacting the (meth)acryloyl-functional support of Formula (II) with a monomer composition that contains a monomer of Formula (III)

$$Z^1-Y^2-CR^2=CH_2 \quad (III)$$

to form a grafted support of Formula (IV).

(IV)

The group $U^1$ includes at least one divalent monomeric unit of formula —$CR^2(Y^2Z^1)$—$CH_2$. Group $U^2$ is hydrogen or is a group that includes at least one divalent monomeric unit of formula —$CR^2(Y^2Z^1)$—$CH_2$—. The group $Y^2$ is a second linking group selected from a single bond or a divalent group that contains an alkylene, heteroalkylene, arylene, or combination thereof. Group $Z^1$ is a functional group selected from (1) an acidic group or a salt thereof, (2) an amino group or a salt thereof, (3) a hydroxyl group, (4) an azlactone group or a precursor of the azlactone group, (5) a glycidyl group, or (6) a combination thereof. The method yet further includes reacting the functional group $Z^1$ of the grafted support with a modifying agent of formula A-T to form a modified grafted support of Formula (V).

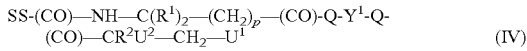

(V)

In Formula (V), the group $U^3$ includes at least one divalent monomeric unit of formula —$CR^2(Y^2$-L-T)-$CH_2$—. Group $U^4$ is selected from hydrogen or a group that includes at least one divalent monomeric unit of formula —$CR^2(Y^2$-L-T)-$CH_2$—. Group L is an attachment group formed by reacting group $Z^1$ on the grafted support with a modifying group A of the modifying agent. Group T is a remainder of the modifying agent A-T and is equal to the modifying agent A-T minus the modifying group A.

In a fifth aspect, an article is provided that includes a modified grafted support of Formula (V).

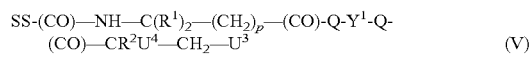

(V)

In Formula (V), SS is a solid support and $R^1$ is each independently selected from alkyl, heteroalkyl, aryl, or aralkyl. The group $R^2$ is hydrogen or an alkyl. The variable p is an integer equal to 0 or 1. Each group Q is independently a divalent group selected from oxy, thio, or —$NR^3$— where $R^3$ is hydrogen, alkyl, heteroalkyl, aryl, or aralkyl. The group $Y^1$ is a first linking group containing an alkylene, heteroalkylene, arylene, or combination thereof. The group $U^3$ includes at least one divalent monomeric unit of formula —$CR^2(Y^2$-L-T)-$CH_2$—. Group $U^4$ is selected from hydrogen or a group that includes at least one divalent monomeric unit of formula —$CR^2(Y^2$-L-T)-$CH_2$—. Group L is an attachment group formed by reacting a group $Z^1$ with a modifying group A of a modifying agent of formula A-T. Group T is a remainder of the modifying agent and is equal to the modifying agent A-T minus the modifying group A. Group $Z^1$ is a functional group selected from (1) an acidic group or a salt thereof, (2) an amino group or a salt thereof, (3) a hydroxyl group, (4) an azlactone group or a precursor of the azlactone group, (5) a glycidyl group, or (6) a combination thereof.

In a sixth aspect, a method of purifying or separating a target compound is provided. The method includes providing an article that includes a grafted support of Formula (IV) as described above. The method further includes contacting the article with a sample containing the target compound such that the target compound interacts with or reacts with at least one functional group $Z^1$ on the grafted support.

In a seventh aspect, another method of purifying or separating a target compound is provided. The method includes providing an article that includes a modified grafted support of Formula (V) as described above. The method further includes contacting the article with a sample containing a target compound such that the target compound interacts with or reacts with at least one group T of the modified grafted support.

The above summary of the present invention is not intended to describe each embodiment or every implementation of the present invention. The Detailed Description and Examples that follow more particularly exemplify these embodiments.

DETAILED DESCRIPTION OF THE INVENTION

Articles that contain a solid support and a grafted chain extending from the solid support, methods of making these articles, and various uses of these articles are described. More specifically, the grafted chain has a functional group that can react with or interact with a target compound. Alternatively, the functional group on the grafted chain can react with a modifying agent to provide another group that can react with or interact with the target compound. The reaction or interaction with the target compound can be used, for example, to purify the target compound or to separate the target compound from other molecules in a sample. In at least some embodiments, the binding capacity for the target compound can be improved through the positioning of the functional group on the grafted chain rather than on a surface of the solid support.

As used herein, the terms "a", "an", and "the" are used interchangeably with "at least one" to mean one or more of the elements being described.

The term "azlactone group" refers to a monovalent group of formula

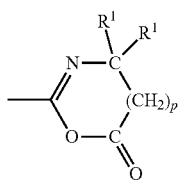

where each $R^1$ is independently selected from alkyl, heteroalkyl, aryl, or aralkyl and the variable p is selected from zero or one. In many embodiments, $R^1$ is methyl. The azlactone group may be referred to as "Az" herein.

The term "precursor of the azlactone group" refers to a group that can undergo a ring closure reaction to form the azlactone group and is of formula —(CO)—NH—C($R^1$)$_2$—(CH$_2$)$_p$—COOH or a salt thereof where $R^1$ and p are defined above for the azlactone group. For example, N-acryloylmethylalanine can be polymerized and then subjected to a ring closure reaction to provide a polymeric material with azlactone groups. In N-acryloylmethylalanine, the precursor of the azlactone group is —(CO)—NH—C(CH$_3$)$_2$—COOH or a salt thereof.

The term "alkyl" refers to a monovalent hydrocarbon group that is saturated and has up to 18 carbon atoms. The alkyl group can be linear, branched, cyclic, or a combination thereof. In some examples, the alkyl group is linear or branched and has 1 to 12 carbon atoms, 3 to 12 carbon atoms, 1 to 10 carbon atoms, 1 to 8 carbon atoms, 1 to 6 carbon atoms, 3 to 6 carbon atoms, 1 to 4 carbon atoms, or 1 to 3 carbon atoms. In other examples, the alkyl is cyclic (i.e., the alkyl is a cycloalkyl) and has 3 to 12 carbon atoms, 3 to 6 carbon atoms, or 4 to 6 carbon atoms.

The term "alkylene" refers to a divalent hydrocarbon group that is saturated and that has up to 18 carbon atoms. The alkylene group can be linear, branched, cyclic, or a combination thereof. In some examples, the alkylene group is linear or branched and has 1 to 12 carbon atoms, 1 to 10 carbon atoms, 1 to 8 carbon atoms, 1 to 6 carbon atoms, 1 to 4 carbon atoms, or 1 to 3 carbon atoms. In other examples, the alkylene is cyclic (i.e., the alkyl is a cycloalkyl) and has 3 to 12 carbon atoms, 3 to 6 carbon atoms, or 4 to 6 carbon atoms.

The term "heteroalkyl" refers to a monovalent group that is saturated and that has at least two carbon atoms separated by at least one catenary heteroatom selected from oxygen (i.e., oxy), sulfur (i.e., thio), or —$NR^3$— where $R^3$ is hydrogen, alkyl, heteroalkyl, aryl, or aralkyl. The heteroalkyl group can be linear, branched, cyclic, or a combination thereof. In some examples, the heteroalkyl group has 2 to 18 carbon atoms and 1 to 6 heteroatoms, 2 to 12 carbon atoms and 1 to 6 heteroatoms, 2 to 10 carbon atoms and 1 to 5 heteroatoms, 2 to 8 carbon atoms and 1 to 4 heteroatoms, or 2 to 6 carbon atoms and 1 to 3 heteroatoms.

The term "heteroalkylene" refers to a divalent group that is saturated and that has at least two carbon atoms separated by at least one catenary heteroatom selected from oxygen (i.e., oxy), sulfur (i.e., thio), or —$NR^3$— where $R^3$ is hydrogen, alkyl, heteroalkyl, aryl, or aralkyl. The heteroalkylene group can be linear, branched, cyclic, or a combination thereof. In some examples, the heteroalkylene group has 2 to 18 carbon atoms and 1 to 6 heteroatoms, 2 to 12 carbon atoms and 1 to 6 heteroatoms, 2 to 10 carbon atoms and 1 to 5 heteroatoms, 2 to 8 carbon atoms and 1 to 4 heteroatoms, or 2 to 6 carbon atoms and 1 to 3 heteroatoms.

The term "aryl" refers to a heterocyclic or carbocyclic monovalent aromatic group. An aryl can have one or more connected or fused rings. Some exemplary aryl groups have a 5 to 12 membered ring structure with 0 to 3 heteroatoms selected from oxygen (i.e., oxy), sulfur (i.e., thio), or —$NR^3$— where $R^3$ is hydrogen, alkyl, heteroalkyl, aryl, or aralkyl. For example, the aryl group can have 2 to 12 carbon atoms and 0 to 3 heteroatoms, 3 to 12 carbon atoms and 0 to 2 heteroatoms, or 4 to 12 carbon atoms and 0 to 1 heteroatoms.

The term "arylene" refers to a heterocyclic or carbocyclic divalent aromatic group. An arylene can have one or more connected or fused rings. Some exemplary arylene groups have a 5 to 12 membered ring structure with 0 to 3 heteroatoms selected from oxygen (i.e., oxy), sulfur (i.e., thio), or —$NR^3$— where $R^3$ is hydrogen, alkyl, heteroalkyl, aryl, or aralkyl.

The term "aralkyl" refers to an alkyl group that is substituted with an aryl group. An aralkyl group can have, for example, 3 to 15 carbon atoms and 0 to 3 heteroatoms, 4 to 15 carbon atoms and 0 to 2 heteroatoms, or 5 to 15 carbon atoms and 0 to 1 heteroatoms.

The term "carbonyl" refers to a divalent group of formula —(CO)— with a double bond between the carbon and oxygen.

The term "carbonyloxy" refers to a divalent group of formula —(CO)—O— where (CO) refers to a carbonyl group.

The term "carbonylthio" refers to a divalent group of formula —(CO)—S— where (CO) refers to a carbonyl group.

The term "carbonylimino" refers to a divalent group of formula —(CO)—$NR^3$— where $R^3$ is hydrogen, alkyl, heteroalkyl, aryl, or aralkyl.

The term "glycidyl" refers to a monovalent group of formula

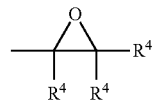

where each $R^4$ is independently a hydrogen, alkyl, heteroalkyl, aryl, or aralkyl. In many glycidyl groups, each $R^4$ is hydrogen.

The term "(meth)acryloyl" refers to a group of formula H$_2$C=$CR^b$—(CO)— where $R^b$ is hydrogen or alkyl (e.g., methyl).

The term "(meth)acrylamido" refers to a group of formula H$_2$C=$CR^b$—(CO)—$NR^a$— where $R^b$ is hydrogen or alkyl (e.g., methyl) and $R^a$ is hydrogen, alkyl, heteroalkyl, aryl, or aralkyl.

The term "(meth)acryloxy" refers to a group of formula H$_2$C=$CR^b$—(CO)—O— where $R^b$ is hydrogen or alkyl (e.g., methyl).

The term "nucleophilic group" refers to a hydroxyl group (i.e., —OH), thiol group (i.e., —SH), primary amino group (i.e., —NH$_2$), or secondary amino group of formula —$NHR^a$ wherein $R^a$ is an alkyl, heteroalkyl, aryl, or aralkyl.

The terms "polymer" or "polymeric" refer to a material that is a homopolymer, copolymer, terpolymer, or the like. Likewise, the terms "polymerize" or "polymerization" refer to the process of making a homopolymer, copolymer, terpolymer, or the like.

The phrase "in the range of" includes the endpoints of the range and all the numbers between the endpoints. For example, the phrase in the range of 1 to 10 includes 1, 10, and all numbers between 1 and 10. Further, any recitation of a range that is not specifically called a range includes the endpoint and all number between the endpoints unless specifically stated otherwise.

The phrase "and/or" means either of the options listed or both of the options listed. For example, the expression A and/or B means A alone, B alone, or both A and B.

The articles are prepared from an azlactone-functionalized support, which is a solid support having at least one azlactone group on a surface of the solid support. Any known azlactone-functionalized support can be used. At least one azlactone group of the azlactone-functionalized support is reacted to form a (meth)acryloyl-functionalized support. The (meth)acryloyl group of the (meth)acryloyl-functional functionalized support can be polymerized with other ethylenically unsaturated monomers to form the grafted chains. The grafted chains are covalently attached to the solid support through a ring opened azlactone group. The grafted chains include a functional group selected from (1) an acidic group or a salt thereof, (2) an amino group or a salt thereof, (3) a hydroxyl group, (4) an azlactone group or a precursor of the azlactone group, (5) a glycidyl group, or (6) a combination thereof. In some embodiments, the functional group is capable of reacting with or interacting with a target compound. In other embodiments, the functional group is modified to form another group that is capable of reacting with or interacting with the target compound. The functional group is modified by reacting with a modifying agent.

The azlactone-functionalized support is of Formula (I).

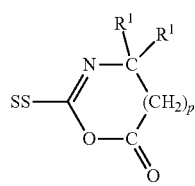

(I)

In Formula (I), SS refers to a solid support, the variable p is an integer equal to zero or one, and each $R^1$ is independently selected from alkyl, heteroalkyl, aryl, or aralkyl. Although Formula (I) shows only one azlactone group attached to the solid support for ease of description, multiple azlactone groups are typically attached to the solid support. The azlactone-functionalized support of Formula (I) can be referred to herein with the formula SS-Az.

The solid support with at least one azlactone group on its surface (i.e., an azlactone-functionalized support) can be in the form of a bead, membrane, foam, film, sheet, coating on a substrate, or the like. Azlactone-functionalized supports and methods of making such supports are described, for example, in U.S. Pat. No. 5,336,742 (Heilmann et al.), U.S. Pat. No. 5,403,902 (Heilmann et al.), U.S. Pat. No. 5,344,701 (Gagnon et al.), U.S. Pat. No. 5,993,935 (Rasmussen et al.), U.S. Pat. No. 6,063,484 (Exsted et al.), U.S. Pat. No. 5,292,514 (Capecchi et al.), U.S. Pat. No. 6,548,607 (Halverson et al.), U.S. Pat. No. 5,408,002 (Coleman et al.), U.S. Pat. No. 5,476,665 (Dennison), U.S. Pat. No. 5,510,421 (Dennison et al.), and U.S. Pat. No. 6,794,458 (Haddad et al.).

Suitable azlactone-functionalized supports can be prepared using a variety of methods. In some methods, the azlactone-functionalized support can be prepared using reverse phase suspension polymerization, a technique in which the polymerization reaction occurs within water droplets suspended in the suspending medium. The suspending medium is water immiscible and the monomers are water-soluble.

In one reverse phase polymerization process, the polymerization medium includes at least one alkenyl azlactone and at least one crosslinking monomer in a water miscible cosolvent. The amount of crosslinking affects polymeric properties such as the porosity and the degree of swelling in a solvent. Suitable alkenyl azlactone monomers include, but are not limited to, 2-vinyl-4,4-dimethyl-2-oxazolin-5-one which is commercially available from SNPE, Inc., Princeton, N.J.; 2-isopropenyl-4,4-dimethyl-2-oxazolin-5-one; and 2-vinyl-4,4-dimethyl-1,3-oxazin-6-one. Suitable crosslinking agents include, but are not limited to, ethylenically unsaturated ($\alpha,\beta$-unsaturated) esters such as ethylene(meth)diacrylate and trimethylolpropane tri(meth)acrylate; and ethylenically unsaturated amides such as methylenebis(meth)acrylamide and N,N'-di(meth)acryloyl-1,2-diaminoethane. Additionally, the polymerization medium can include other monomers that are water soluble and that can be polymerized using a free radical addition polymerization reaction. Suitable optional monomers include, for example, N,N-dimethylacrylamide and N-vinylpyrrolidone. This polymerization process is further described in U.S. Pat. No. 5,403,902 (Heilmann et al.) and U.S. Pat. No. 5,336,742 (Heilmann et al.)

In another reverse phase polymerization process, a two-step polymerization process is used to prepare azlactone-functionalized supports. In a first step, polymeric material is prepared that has carboxylic functional groups. The carboxylic functional groups are subsequently reacted with a cyclization agent to form azlactone groups. The polymerization medium includes a water-soluble salt of a N-(meth)acryloylamino acid, a crosslinking monomer, and a water immiscible suspending medium. Additionally, the polymerization medium can include other monomers that are water soluble and that can be polymerized using a free radical addition polymerization reaction. Suitable optional monomers include, for example, N,N-dimethylacrylamide and N-vinylpyrrolidone. Suitable cyclization agents include, for example, acetic anhydride, trifluoroacetic anhydride, and alkyl chloroformates. This process is further described in U.S. Pat. No. 5,403,902 (Heilmann et al.) and U.S. Pat. No. 5,336,742 (Heilmann et al.).

In other methods, the azlactone-functionalized support can be prepared using dispersion polymerization, a technique in which a dispersing medium is chosen that will dissolve the monomers but that will precipitate the polymer as it forms. Various surfactants can be added to prevent aggregation of the polymer particles. For example, the azlactone-functionalized support can be prepared using a dispersion polymerization process in which the polymerization medium includes a 2-alkenyl azlactone monomer, a crosslinking monomer, and at least one surfactant in an organic solvent such as an alcohol. This process is further described in U.S. Pat. No. 5,403,902 (Heilmann et al.) and U.S. Pat. No. 5,336,742 (Heilmann et al.).

The polymeric azlactone-functionalized support can be a gel-type or macroporous polymeric material. As used herein, the term "gel-type" refers to a polymeric material that is prepared with less than 20 weight percent crosslinker based on the weight of monomers in the polymerization medium. As used herein, the term "macroporous" refers to a polymeric material that is prepared with at least 20 weight percent crosslinker based on the weight of monomers in the polymerization medium. A gel-type material tends to swell more and tends to be less rigid than macroporous materials.

In some embodiments, the substrate is the form of a bead. The beads can have a spherical shape, regular shape, or irregular shape. Beads can be prepared using either reverse phase suspension polymerization techniques or dispersion polymerization techniques. Beads that are prepared using reverse phase suspension polymerization techniques tend to be more porous and to have larger surface areas compared to beads that are prepared using dispersion polymerization techniques. Beads prepared using dispersion polymerization techniques are generally smaller in size and are less porous (e.g., in some cases the beads can be substantially nonporous) than beads that are prepared using reverse phase suspension polymerization techniques.

The size of the beads can vary depending on the particular application. Generally, the average diameter of the beads is in the range of 0.1 micrometers to 5 millimeters. Some exemplary beads have an average diameter of 0.1 to 1,000 micrometers, 0.1 to 500 micrometers, 0.1 to 100 micrometers, 0.5 to 100 micrometers, 0.1 to 50 micrometers, 0.1 to 20 micrometers, 0.1 to 3 micrometers, or 0.5 to 3 micrometers.

In some methods of making an azlactone-functionalized support, the substrate is in the form of a composite membrane that includes azlactone-containing particles (e.g., beads) dispersed in a continuous, porous matrix. Such composite membranes are further described in U.S. Pat. No. 5,993,935 (Rasmussen et al.). The azlactone-containing particles included in the composite membrane can be the beads described above. Alternatively, the azlactone-containing particles included in the membranes can be inorganic particles modified with a coating composition to provide a surface with azlactone groups. The inorganic particles can contain, for example, metals or metal oxides, ceramic materials such as alumina, silica, zirconia, or mixtures thereof, glass (e.g., beads or bubbles), controlled pore glass, and the like. These particles can be modified by coating the particles with a polymer that contains reactive azlactone functional groups or by reacting groups on the surface of the particles with a reagent that contains a reactive functional group (e.g., a coupling agent that has an alkoxy silane for reacting with the surface of the inorganic particle and that also contains an azlactone group).

Useful continuous, porous matrices for the composite membrane include, but are not limited to, woven and nonwoven fibrous webs or porous fibers. Exemplary fibrous materials include those fabricated from polyolefins (e.g., polyethylene and polypropylene), polyvinyl chloride, polyamides (e.g., nylons), polystyrenes, polysulfones, polyvinyl alcohol, polybutylene, ethyl vinyl acetate, poly(meth)acrylates such as polymethyl methacrylate, polycarbonate, cellulosics (e.g., cellulose acetate), polyesters (e.g., polyethylene terephthalate), polyimides, polyurethanes (e.g., polyether polyurethanes), and combinations thereof.

In another method of preparing a composite membrane, azlactone-containing particles are dispersed in a liquid to form a colloidal suspension. A thermoplastic polymer is melt blended with the colloidal suspension at a temperature sufficient to form a homogenous solution. The solution can be formed into a desired shape and then cooled to induce phase separation of the liquid from the polymeric material and solidify the polymeric material. After removal of the liquid, the azlactone-containing particles are dispersed in a microporous polymer matrix. This method is described in detail in U.S. Pat. No. 4,957,943 (McAllister et al.).

The composite membranes can also be prepared from a porous fibrillated polymer matrix such as fibrillated polytetrafluoroethylene (PTFE). The azlactone-containing particles can be blended with a PTFE dispersion to obtain a putty-like mass. The putty-like mass can then be mixed at a temperature between 5° C. and 100° C. to cause fibrillation of the PTFE and biaxially calendered to form a sheet. The sheet can be dried to remove any solvent. Such methods of making membranes are further described in U.S. Pat. No. 4,153,661 (Ree et al.); U.S. Pat. No. 4,565,663 (Errede et al.); U.S. Pat. No. 4,810,381 (Hagen et al.); and U.S. Pat. No. 4,971,736 (Hagen et al.).

Yet another method of making a composite membrane is described in U.S. Pat. No. 4,539,256 (Shipman). Azlactone-containing particles can be dispersed in a polyolefin by heating and stirring. The resulting molten mixture is cast onto a heated plate, subjected to pressure, and then cooled in ice water.

Additionally, composite membranes can also be formed using solvent phase inversion techniques as described in U.S. Pat. No. 5,476,665 (Dennison). An azlactone-containing particle and blending polymers are introduced into a vessel containing a solvent capable of dissolving the polymers, casting the solution into a desired shape, and introducing the cast shape to a coagulation bath of a liquid that is miscible with the solvent but in which the polymers precipitate to form an azlactone-functionalized membrane.

Azlactone-functionalized supports can also be formed from polymer blends as described in U.S. Pat. No. 5,408,002 (Coleman et al.) and U.S. Pat. No. 6,063,484 (Exsted et al.). Azlactone-containing homopolymers prepared from 2-alkenyl azlactone can be melt blended with thermoplastic polymers. Suitable thermoplastics include polyamides (e.g., nylon 6), polyurethanes, poly(meth)acrylates, polystyrene, polyolefins, ethylene vinyl acetate copolymers, poly(N-vinyl lactams) (e.g., polyvinyl pyrrolidone), polyvinyl acetate, polyoxyalkylene oxides, fluoroelastomers, polycarbonates, polyesters, and the like.

Another method of preparing azlactone-functionalized substrates is described in U.S. Pat. No. 6,063,484 (Exsted et al.). A polyolefin resin is mixed with a free radical initiator (e.g., a peroxide or azo compound) and then heated in an extruder at a temperature sufficient to generate free radicals. A 2-alkenyl azlactone is injected into the extruder to form a grafted azlactone thermoplastic composition. This composition is then formed into a membrane.

Alternatively, azlactone-functionalized supports can be formed using solvent phase inversion of an azlactone-containing polymer as described in U.S. Pat. No. 5,510,421 (Dennison et al.). Azlactone-containing compositions and blending polymers are placed in a vessel containing a solvent capable of dissolving them. The solution is then cast into a suitable shape, which is then introduced into a coagulation bath of a liquid miscible with the solvent but that causes the precipitation of an azlactone-functionalized membrane.

An azlactone-functionalized support can also be prepared by applying a coating composition to a solid support. Exemplary solid supports can be prepared from metal, metal oxide or hydroxide, polymeric material, glass, ceramic material, or a combination thereof. The solid support can have any desired shape or size. For example, the supports can be films, particles, fibers, woven or nonwoven webs, membranes, molded plastic articles, and the like. In some embodiments, the coating composition can include a soluble polymer having azlactone groups (e.g., a polymer formed by free radical polymerization of an alkenyl azlactone monomer) and a crosslinking agent. The coating composition can be applied to the solid support using techniques such as extrusion coating, die coating, dip coating, air-knife coating, gravure coating, curtain coating, spray coating, and the like. This process is further described in U.S. Pat. No. 6,794,458 (Haddad et al.). In other embodiments, a surface of a solid support is coated with a coating composition that includes azlactone-functional monomers and crosslinking monomers. The coating composition is polymerized to form an azlactone-functional surface layer on the solid support. This embodiment is further described in U.S. Pat. No. 5,344,701 (Gagnon et al.).

In some examples, there is sufficient adhesion of the coating composition containing the soluble polymer having azlactone groups to the surface of the solid support. With other solid supports, the adhesion can be enhanced by various pretreatments such as plasma or corona treatment of the solid support or by using a primer layer between the solid support and the coating composition.

Polymeric beads with azlactone groups are commercially available under the trade designation "EMPHAZE" from 3M Company, St. Paul, Minn.

The azlactone-functionalized support of Formula (I) is reacted to form a a (meth)acryloyl-functionalized support of Formula (II).

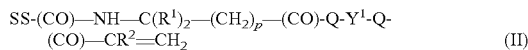

$$SS\text{-}(CO)\text{-}NH\text{-}C(R^1)_2\text{-}(CH_2)_p\text{-}(CO)\text{-}Q\text{-}Y^1\text{-}Q\text{-}(CO)\text{-}CR^2\!\!=\!\!CH_2 \quad (II)$$

In Formula (II), SS refers to the solid support. Group $R^1$ and variable p are the same as described above for Formula (I). Each group Q is independently a divalent group selected from oxy, thio, or —$NR^3$— where $R^3$ is a hydrogen, alkyl, heteroalkyl, aryl, or aralkyl. Group $R^2$ is typically hydrogen or an alkyl. Group $Y^1$ in Formula (II) is a first linking group that contains an alkylene, heteroalkylene, arylene, or combination thereof. The group $Y^1$ can further contain other optional groups that link together two or more alkylene groups, heteroalkylene groups, arylene groups, or combinations thereof. The optional groups can include, for example, a carbonyl, carbonyloxy, carbonylthio, carbonylimino, oxy, thio, —$NR^3$—, or combination thereof.

The (meth)acryloyl-functionalized support of Formula (II) can be prepared from the azlactone-functionalized support of Formula (I) using any known synthesis method. In one exemplary method, the azlactone-functionalized support of Formula (I) is reacted with a compound having both (a) a nucleophilic group and (b) a (meth)acryloyl group. For example, the compound can be of Formula (VI).

$$HQ\text{-}Y^1\text{-}Q\text{-}(CO)\text{-}CR^2\!\!=\!\!CH_2 \quad (VI)$$

In Formula (VI), $Y^1$ and Q are the same as described above for Formula (II). The group -QH, which corresponds to —OH, —SH, or —$NR^3$H, is the nucleophilic group that can react with an azlactone group of the azlactone-functionalized support. This reaction results in the opening of the azlactone ring.

Exemplary compounds of Formula (VI) where the group -QH is a hydroxyl group include, but are not limited to, hydroxyalkyl(meth)acrylates such as 2-hydroxyethyl(meth)acrylate, 2-hydroxypropyl(meth)acrylate, 3-hydroxypropyl (meth)acrylate, 4-hydroxybutyl(meth)acrylate, glycerol (meth)acrylate, and glycerol di(meth)acrylate; and hydroxyalkyl(meth)acrylamides such as hydroxypropyl (meth)acrylamide and methylol(meth)acrylamide.

Exemplary compounds of Formula (VI) where the group -QH is a primary or secondary amino group include, but are not limited to, aminoalkyl(meth)acrylamides such as aminoethyl(meth)acrylamide and aminopropyl(meth)acrylamide; N-alkylaminoalkyl(meth)acrylamides such as N-methylaminoethyl(meth)acrylamide and N-isopropylaminopropyl (meth)acrylamide; aminoalkyl(meth)acrylates such as aminoethyl(meth)acrylate, aminopropyl(meth)acrylate; and N-alkylaminoalkyl(meth)acrylates such as N-methylaminoethyl(meth)acrylate and N-methylaminopropyl(meth)acrylate.

The reaction of the azlactone-functionalized support of Formula (I) with the compound of Formula (VI) is shown in Reaction Scheme A where the group "Az" represents an azlactone group and the group "$Az^1$" represents a ring-opened azlactone group. As used herein, the ring-opened azlactone group $Az^1$ is a divalent group of formula —(CO)—NH—C $(R^1)_2$—$(CH_2)_p$—(CO)—. The (meth)acryloyl-functionalized support of Formula (II) can be written using the formula $SS\text{-}Az^1\text{-}Q\text{-}Y^1\text{-}Q\text{-}(CO)\text{-}CR^2\!\!=\!\!CH_2$.

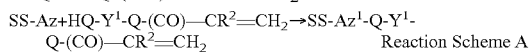

$$SS\text{-}Az\text{+}HQ\text{-}Y^1\text{-}Q\text{-}(CO)\text{-}CR^2\!\!=\!\!CH_2 \rightarrow SS\text{-}Az^1\text{-}Q\text{-}Y^1\text{-}Q\text{-}(CO)\text{-}CR^2\!\!=\!\!CH_2 \quad \text{Reaction Scheme A}$$

In another exemplary method of preparing the (meth)acryloyl-functionalized support of Formula (II), the azlactone-functionalized support of Formula (I) is reacted with a nucleophilic compound having at least two nucleophilic groups selected from a hydroxyl group (—OH), thiol group (—SH), primary amino group (—$NH_2$), or secondary amino group (—$NHR^3$). A first nucleophilic group can react with an azlactone group of the azlactone-functionalized support of Formula (I). This reaction opens the azlactone ring. The second nucleophilic group can react with another compound such that the product has a (meth)acryloyl group. The compound having two nucleophilic groups can be represented by Formula (VII).

$$HQ\text{-}Y^{1a}\text{-}QH \quad (VII)$$

In Formula (VII), Q is the same as defined previously for Formula (II). Like group $Y^1$, the group $Y^{1a}$ includes an alkylene, heteroalkylene, arylene, or combination thereof and can optionally further include an oxy, thio, amino (—$NR^3$—), carbonyloxy, carbonylthio, carbonylimino, or combination thereof.

Some exemplary nucleophilic compounds of Formula (VII) are alcohol amines (i.e., hydroxyamines) having both a hydroxyl group and a primary or secondary amino group. Exemplary alcohol amines include, but are not limited to, 2-hydroxyethylamine, 3-hydroxypropylamine, 4-hydroxybutylamine, 1,2-dihydroxy-3-aminopropane, 1-hydroxy-6-aminohexane, bis-(2-hydroxyethyl)amine, triethanolamine, 1-amino-3,5-dihydroxycyclohexane, 1-amino-3,5-dihydroxybenzene, N,N'-bis(2-hydroxyethyl)piperazine, N-hydroxyethylpiperazine, 2-amino-2-methyl-1,3-propanediol, and the like. Other exemplary nucleophilic compounds of Formula (VI) have at least two primary or secondary amino groups such as hydrazine, adipic dihydrazide, ethylenediamine, N-methylethylenediamine, piperazine, N-(2-aminoethyl)-piperazine, 1,3-propanediamine, 1,4-butanediamine, benzenediamine, m-xylylenediamine, 1,3-cyclohexane-bismethylamine, 1,4-cyclohexanediamine, 1,8-diamino-3,6-dioxaoctane, 1,3-diamino-2-hydroxypropane, tris-(2-aminoethyl)amine, and 1,6-hexanediamine. Additional nucleophilic compounds with at least two amino groups are polyether amines such as those commercially available under the trade designation JEFFAMINE from Huntsman Corporation (The Woodlands, Tex.). Still other exemplary nucleophilic compounds of Formula (VI) are compounds with two or more hydroxyl groups such as ethylene glycol, diethylene glycol, triethylene glycol, 1,2-propanediol, 1,3-propanediol, 1,2-butanediol, 1,3-butanediol, 1,4-butanediol, glycerol, trimethylolpropane, pentaerythritol, dihydroxybenzene, trihydroxybenzene, and bisphenol A. Additional nucleophilic compounds with at least two hydroxyl groups are polyethylene oxides and polypropylene oxides having hydroxyl end groups.

The reaction of the azlactone-functionalized support of Formula (I) with a nucleophilic compound of Formula (VII) results in the opening of the azlactone ring as shown in the intermediate of Formula (VIII)

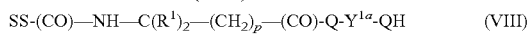

$$SS\text{-}(CO)\text{-}NH\text{-}C(R^1)_2\text{-}(CH_2)_p\text{-}(CO)\text{-}Q\text{-}Y^{1a}\text{-}QH \quad (VIII)$$

that can also be represented by the formula SS-Az$^1$-Q-Y$^{1a}$-QH. This intermediate of Formula (VIII) can then be reacted with a second compound such that the product has a (meth)acryloyl group. The second compound can have a first group capable of reacting with the nucleophilic group -QH of the intermediate and a second group that is ethylenically unsaturated. For example, the intermediate can react with a second compound that is a vinyl azlactone (e.g., vinyl dimethyl azlactone), acyl halide having a (meth)acryloyl group, anhydride having a (meth)acryloyl group, isocyanatoalkyl(meth)acrylate such as isocyanatoethyl(meth)acrylate, or glycidyl(meth)acrylate. This method is exemplified in Reaction Scheme B for a second compound that is a vinyl azlactone of formula Az-CR$^2$=CH$_2$.

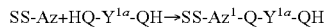

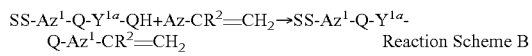 Reaction Scheme B

The formula SS-Az$^1$-Q-Y$^{1a}$-Q-Az$^1$-CR$^2$=CH$_2$ corresponds to SS-AZ$^1$-Q-Y$^{1a}$Q-(CO)—(CH$_2$)$_p$—C(R$^1$)$_2$—NH—(CO)—CR$^2$=CH$_2$, which in turn corresponds to Formula (II) where Y$^1$ is equal to —Y$^{1a}$-Q-(CO)—CH$_2$)$_p$—C(R$^1$)$_2$— and where one of the Q groups is an amino group.

The (meth)acryloyl-functionalized support of Formula (II) can then be reacted with a monomer composition that contains a functional monomer of Formula (III).

 (III)

In Formula (III), group Y$^2$ is a second linking group selected from a single bond or a divalent group that contains an alkylene, heteroalkylene, arylene, or combination thereof. The group Y$^2$ can further contain other optional groups that function to connect two or more alkylenes, heteroalkylenes, arylenes, or mixtures thereof. The optional groups can include, for example, a carbonyl, carbonyloxy, carbonylthio, carbonylimino, oxy, thio, —NR$^3$—, or combination thereof. Group Z$^1$ is a first functional group selected from (1) an acidic group or a salt thereof, (2) an amino group or a salt thereof, (3) a hydroxyl group, (4) an azlactone group or a precursor to the azlactone group, (5) a glycidyl group, or (6) a combination thereof. Groups R$^2$ and R$^3$ are the same as described above for Formula (II).

The functional monomer of Formula (III) has both an ethylenically unsaturated group capable of undergoing a free radical polymerization reaction plus a functional group Z$^1$. The functional monomer of Formula (III) undergoes a free radical polymerization reaction with the (meth)acryloyl-functionalized support of Formula (II) resulting in the formation of a grafted support that includes a grafted chain extending from the solid support. In many embodiments, the solid support has multiple grafted chains. The grafted chain includes at least one divalent monomeric unit of formula —CR$^2$(Y$^2$Z$^1$)—CH$_2$—. The grafted chain is often polymeric and contains at least two or at least three monomeric units of formula —CR$^2$(Y$^2$Z$^1$)—CH$_2$—. The grafted chains have at least one pendant group of formula —Y$^2$—Z$^1$. If the grafted chain is polymeric, the grafted chain contains at least two or at least three pendant groups of formula —Y$^2$Z$^1$.

In some embodiments, the functional monomer of Formula (III) has a (meth)acrylolyl group as shown in Formula (Ma).

 (IIIa)

The group Y$^{2a}$ is a divalent group that includes an alkylene, heteroalkylene, arylene, or combination thereof and optionally can include an oxy, thio, amino, carbonylimino, carbonyloxy, carbonylthio, or a combination thereof.

The group Z$^1$ of the functional monomers of Formula (III) or (IIIa) can be an acidic group or a salt thereof. The functional monomer can be a weak acid, a salt of a weak acid, a strong acid, a salt of a strong acid, or a combination thereof. The functional monomer can be in a neutral state but capable of being negatively charged if the pH is adjusted. Some exemplary functional monomers of Formulas (III) or (IIIa) are sulfonic acids or salts thereof such as (meth)acrylamidosulfonic acids or salts thereof. More specific (meth)acrylamidosulfonic acids include, but are not limited to, N -(meth)acrylamidomethanesulfonic acid, 2-(meth)acrylamidoethanesulfonic acid, and 2-(meth)acrylamido-2-methylpropanesulfonic acid. Salts of these acidic monomer can also be used. Some other exemplary functional monomers having an acid group or salt thereof include other sulfonic acids such as vinylsulfonic acid, 3-sulfopropyl(meth)acrylate, sulfoethyl(meth)acrylate, and 4-styrenesulfonic acid.

Still other exemplary functional monomers having an acid group include, but are not limited to, phosphonic acids or salts thereof or carboxylic acids or salts thereof. For example, the function monomers can be (meth)acrylamidoalkylphosphonic acids such as 2-(meth)acrylamidoethylphosphonic acid and 3-(meth)acrylamidopropylphosphonic acid; acrylic acid and methacrylic acid; and carboxyalkyl(meth)acrylates such as 2-carboxyethyl(meth)acrylate and 3-carboxypropyl(meth)acrylate. Still other suitable monomers include (meth)acryloylamino acids, such as those described in U.S. Pat. No. 4,157,418 (Heilmann). Exemplary (meth)acryloylamino acids include, but are not limited to, N-(meth)acryloylglycine, N-(meth)acryloylaspartic acid, N-(meth)acryloyl-β-alanine, and N-(meth)acryloyl-2-methylalanine. Salts of any of these acidic monomers can also be used. If the functional monomer is in the form of a salt of a weak acid or a salt of a strong acid, the counter ion of these salts can be, but are not limited to, alkali metal ions, alkaline earth metal ions, ammonium ions, or tetraalkylammonium ions.

A second type of functional monomer of Formula (III) or (IIIa) has an amino group or a salt thereof for Z$^1$. The amino group or salt thereof can be a primary amino group, secondary amino group, tertiary amino group, or quaternary ammonium group. This type of functional monomer can be a weak base, a strong base, a salt of a weak base, a salt of a strong base, or a mixture thereof. The functional monomer can be in a neutral state but capable of being positively charged if the pH is adjusted. If the functional monomer is in the form of a salt, the counter ion can be, but is not limited to, a halide (e.g., chloride), a carboxylate (e.g., acetate or formate), nitrate, phosphate, sulfate, bisulfate, methyl sulfate, or hydroxide.

Some exemplary functional monomers having an amino group or salt thereof include amino(meth)acrylates or amino (meth)acrylamides (as well as quaternary ammonium salts thereof) as shown in Formula (IIIb)

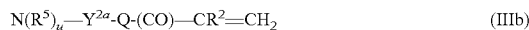 (IIIb)

In Formula (IIIb), Y$^{2a}$, Q, y and R$^2$ are the same as described above for Formula (III) or (IIIa). Each R$^5$ is independently hydrogen, alkyl, hydroxyalkyl (i.e., an alkyl substituted with a hydroxy), aminoalkyl (i.e., an alkyl substituted with an amino), aryl, or aralkyl. The variable u is equal to 2 for a primary, secondary, or tertiary amino group and equal to 3 for quaternary amino group. When u is equal to 3, the three R$^5$ groups are independently selected from alkyl, hydroxyalkyl, aminoalkyl, aryl, or arylalkyl. That is, R$^5$ typically is not equal to hydrogen when the variable u is equal to 3.

When the variable u is equal to 2, the $R^5$ groups in Formula (IIIb) taken together with the nitrogen atom to which they are attached can form a heterocyclic group that is aromatic, partially unsaturated (i.e., unsaturated but not aromatic), or saturated. Such a heterocyclic group can optionally be fused to a second ring that is aromatic (e.g., benzene), partially unsaturated (e.g., cyclohexene), or saturated (e.g., cyclohexane). The counter ions of the quaternary ammonium salts are often halides, sulfates, phosphates, nitrates, and the like.

In some embodiments of Formula (IIIb) where the variable u is equal to 2, both $R^5$ groups are hydrogen. In other embodiments where the variable u is equal to 2, one $R^5$ group is hydrogen and the other is an alkyl having 1 to 10, 1 to 6, or 1 to 4 carbon atoms. In still other embodiments where the variable u is equal to 2, at least one of $R^5$ groups is a hydroxyl alkyl or an amino alkyl that has 2 to 10, 2 to 6, or 2 to 4 carbon atoms with the hydroxyl or amino group positioned on any of the carbon atoms of the alkyl group except the first. In still other embodiments where the variable u is equal to 2, at least one of the $R^5$ groups is an aryl having 5 or 6 carbon atoms; or an aralkyl with the alkyl group having 1 to 10 carbon atoms and the aryl group having 5 or 6 carbon atoms. In yet other embodiments, the two $R^5$ groups combine with the nitrogen atom to which they are attached to form a heterocyclic group. The heterocyclic group includes at least one nitrogen atom and can contain other heteroatoms such as oxygen or sulfur. Exemplary heterocyclic groups include, but are not limited to, imidazolyl, piperazinyl, and morpholinyl. The heterocyclic group can be fused to an additional ring such as a benzene, cyclohexene, or cyclohexane. Exemplary heterocyclic groups fused to an additional ring include, but are not limited to, benzimidazolyl.

Exemplary amino(meth)acrylates of Formula (IIIb) where Q is oxy include, but are not limited to, N,N-dialkylaminoalkyl(meth)acrylates such as, for example, N,N-dimethylaminoethyl(meth)acrylate, N,N-diethylaminoethyl(meth)acrylate, N,N-dimethylaminopropyl(meth)acrylate, N-tert-butylaminopropyl(meth)acrylate, and the like.

Exemplary amino(meth)acrylamides of Formula (IIIb) where Q is —NH— include, but are not limited to, N-(3-aminopropyl)(meth)acrylamide, N-[3-(dimethylamino)propyl](meth)acrylamide, N-(3-imidazolylpropyl)(meth)acrylamide, N-(2-imidazolylethyl)(meth)acrylamide, N-(1,1-dimethyl-3-imidazoylpropyl)(meth)acrylamide, and N-(3-benzimidazolylpropyl)(meth)acrylamide.

Exemplary quaternary salts of the functional monomers of Formula (IIIb) include, but are not limited to, (meth)acrylamidoalkyltrimethylammonium salts such as (meth)acrylamidopropyltrimethylammonium chloride; and (meth)acryloxyalkyltrimethylammonium salts such as 2-(meth)acryloxyethyltrimethylammonium chloride, and 2-(meth)acryloxyethyltrimethylammonium methyl sulfate.

A third type of functional monomer of Formula (III) or (IIIa) has a hydroxyl $Z^1$ group. Suitable hydroxy-containing monomers include hydroxy substituted alkyl(meth)acrylates, hydroxy substituted alkyl(meth)acrylamides, or vinyl alcohols. Specific hydroxy-containing monomers include, but are not limited to, 2-hydroxyethyl(meth)acrylate, 3-hydroxylpropyl(meth)acrylate, 4-hydroxybutyl(meth)acrylate, glycerol(meth)acrylate, N-[tris(hydroxymethyl)methyl]acrylamide, vinyl benzylalcohol, and hydroxyethyl(meth)acrylamide.

A fourth type of functional monomer of Formula (III) or (IIIa) has an azlactone $Z^1$ group. Exemplary functional monomers having an azlactone group include, but are not limited to, vinyl alkylazlactones such as 2-vinyl-4,4-dimethylazlactone (also called 2-vinyl-4,4-dimethyl-2-oxazolin-5-one), 2-(4-vinylphenyl)-4,4-dimethylazlactone, 2-isopropenyl-4,4-dimethylazlactone, 2-vinyl-4-ethyl-4-methyl-2-oxazolin-5-one, and 2-vinyl-4,4-dimethyl-1,3-oxazin-6-one. A further embodiment of the fourth type of functional monomer has a precursor group of the azlactone group as the $Z^1$ group. The precursor group can be subjected to a ring closure reaction to form the azlactone group. Exemplary functional monomers that can provide this precursor group include, but are not limited to, N-acryloylmethylalanine.

A fifth type of functional monomer of Formula (III) or (IIIa) has a glycidyl as the $Z^1$ group. Exemplary monomers having a glycidyl group include, but are not limited to, glycidyl(meth)acrylate.

Still other functional monomers have a combination of two or more functional $Z^1$ groups selected from (1) an acidic group or salt thereof, (2) an amino group or salt thereof, (3) a hydroxyl group, (4) an azlactone group, or (5) a glycidyl group. Exemplary functional monomers having multiple and different types of functional groups are 3-(meth)acryloxy-2-hydroxypropyltrimethylammonium chloride and 2-(meth)acrylamidoglycolic acid.

The polymerization of the (meth)acryloyl-functionalized support of Formula (II) with a monomer composition that contains a functional monomer of Formula (III) leads to the formation of the grafted support of Formula (IV).

$$\text{SS-(CO)—NH—C}(R^1)_2\text{—(CH}_2)_p\text{—(CO)-Q-Y}^1\text{-Q-(CO)—CR}^2U^2\text{—CH}_2\text{—U}^1 \quad \text{(IV)}$$

In Formula (IV), SS refers to the solid support. Groups Q, $Y^2$, $Z^1$, $R^1$, p, and $Y^1$ are the same as described for Formulas (II) and (III). Group $U^1$ is a polymeric unit that includes at least one divalent monomeric unit of formula —$CR^2(Y^2Z^1)$—$CH_2$—. Group $U^2$ is hydrogen or a group that includes at least one divalent monomeric unit of formula —$CR^2(Y^2Z^1)$—$CH_2$—. The $Z^1$ groups that are included in group $U^1$ or in both groups $U^1$ and $U^2$ can often react with or interact with a target compound.

The grafted chain can include one or more monomeric units of formula —$CR^2(Y^2Z^1)$—$CH_2$—. In many embodiments, the grafted chain includes at least two or at least three monomeric units. That is, the grafted chain if often polymeric and includes at least two or at least three pendant groups —$Y^2$—$Z^1$.

The groups $U^1$ and $U^2$ can include at least one group of formula —$CR^2(Y^2Z^1)$—$CH_2$—. Often, these groups include at least two or at least three monomeric units of formula —$CR^2(Y^2Z^1)$—$CH_2$— and are considered to be polymeric chains. In a few instances, the group $U^2$ or $U^1$ is a residue of a chain transfer agent used in the polymerization reaction or is a residue of a free radical initiator molecule. If either $U^1$ or $U^2$ is the residue of a chain transfer agent, it is often a halogen such as from tetrabromomethane.

The grafted support can be used to separate and/or purify a target compound. That is, methods of separating or purifying a target compound are provided that include providing a grafted support of Formula (IV) and contacting a sample containing the target compound with the grafted support. The target compound reacts with or interacts with the functional group $Z^1$ of the grafted chain of the grafted support.

In some embodiments of the grafted support of Formula (IV), the grafted chain has a $Z^1$ group that is an acidic group or a salt thereof. The grafted support can function as a cation exchange material. When the pH is suitably adjusted, the $Z^1$ group on the grafted chain can be a negatively charged group capable of interacting with a positively charged group of the target compound (i.e., the target compound is a cation). The target compound can be adsorbed on the grafted support. To release the adsorbed target compound, the pH can be raised (e.g., the pH can be raised to at least 6 or 7 or higher). Alternatively, when the target compound is a biomolecule, the sample can be contacted with and adsorbed on the grafted support in a low ionic strength buffer (e.g., 5 to 150 millimolar (mM) buffer salt plus 0 to 200 millimolar sodium chloride) at a pH of about 3 to 10 or at a pH of about 4 to 6. To release the adsorbed biomolecule, the grafted support can be contacted with a high ionic strength buffer. In some embodiments, the high ionic strength buffer includes that same buffer composition used to adsorb the target compound plus 1 or 2 molar (M) sodium chloride. The adsorption and release processes are typically performed at temperatures near room temperature.

The grafted supports of Formula (IV) can often be used under pH conditions and/or salt conditions that may be unsuitable for some known ion exchange resins. For example, the dynamic binding capacity of the grafted support can have a maximum at a pH that is 0.5 or 1 pH unit higher or lower than many known ion exchange resins. Greater capacity at a higher pH value can be particularly advantageous for the separation or purification of various proteins. Many proteins are sensitive to low pH conditions and many known ion exchange resins tend to be used at pH values that are not optimal for proteins. The grafted supports can be used at higher pH values that are more suitable for some proteins.

Buffer salts useful for controlling the pH for cation exchange reactions include, but are not limited to, sodium phosphate, sodium carbonate, sodium bicarbonate, sodium borate, sodium acetate, and TRIS (tris(hydroxymethyl)aminomethane). Other suitable buffers include "Good's" buffers such as MOPS (3-morpholinopropanesulfonic acid), EPPS (4-(2-hydroxyethyl)piperazine-1-propanesulfonic acid), MES (2-morpholinoethanesulfonic acid), and others.

In other embodiments of the grafted support of Formula (IV), the grafted chain has a $Z^1$ group that is an amino group or a salt thereof. A primary amino group or a secondary amino group can react as a nucleophilic agent with a target compound. Alternatively, the grafted support can function as an anion exchange material. When the pH is suitably adjusted, the grafted support can have a positively charged group capable of interacting with a negatively charged group of the target compound (i.e., the target compound is an anion).

In general, in order to get effective adsorption of the negatively charged target compound to the anion exchange material, a pH of at least about 1 to 2 pH units above the pKa of the target compound (or pI for a protein) can be used. To release the adsorbed target compound from the anion exchange material, if desired, the pH can be lowered at least 1 to 2 pH units, or more. Alternatively, when the charged target compound is a biomolecule, the sample can be contacted with the anion exchange material in a low ionic strength buffer (e.g., a 5 to 20 millimolar buffer salt) at an appropriate pH (e.g., at a pH of about 6-8 for bovine serum albumin). To release the adsorbed biomolecule, the anionic exchange material is often contacted with a high ionic strength buffer. In some embodiments, the high ionic strength buffer includes that same buffer composition used to adsorb the target compound plus 1 molar sodium chloride. The adsorption and release processes are typically performed at temperatures near room temperature.

Buffer salts useful for controlling pH for anion exchange materials include, but are not limited to, sodium phosphate, sodium carbonate, sodium bicarbonate, sodium borate, sodium acetate, and TRIS (tris(hydroxymethyl)aminomethane). Other suitable buffers include "Good's" buffers such as MOPS (3-morpholinopropanesulfonic acid), EPPS (4-(2-hydroxyethyl)piperazine-1-propanesulfonic acid), MES (2-morpholinoethanesulfonic acid), and others.

In still other embodiments of the grafted support of Formula (IV), the grafted chain has a hydroxyl $Z^1$ group. The hydroxyl group on the grafted chain can undergo a condensation reaction with a target compound. For example, a hydroxyl group can react with a target compound having a carboxyl group (—COOH) to form an ester. That is, the reaction results in the formation of a carbonyloxy linkage group that covalently bonds the target compound to the grafted chain. For example, a protein or other molecule can be covalently bonded to the grafted chain. Alternatively, the grafted chains having hydroxyl groups can serve to provide a neutral, hydrophilic, pore-modifying material such that the resin can be used as a size exclusion resin.

In yet other embodiments of the grafted support of Formula (IV), the grafted chain has an azlactone $Z^1$ group. The azlactone group on the grafted chain can undergo a ring-opening reaction with a target compound having a nucleophilic group. Suitable nucleophilic groups for reacting with an azlactone group include, but are not limited to, primary amino groups, secondary amino groups, thiol groups, and hydroxyl groups. The reaction of the azlactone group with a nucleophilic group of the target compound usually results in the formation of a linkage group that attaches the target compound to the grafted chain. The linkage group formed by ring-opening of the azlactone group often contains the group —(CO)NHC($R^1$)$_2$ (CH$_2$)$_p$(CO)—. The reaction of azlactone-functional resins with a variety of nucleophilic compounds (e.g., target compounds) is further described in U.S. Pat. No. 5,292,840 (Heilmann et al.), U.S. Pat. No. 5,561,097 (Gleason et al.), and U.S. Pat. No. 6,379,952 (Rasmussen et al.).

Alternatively, the grafted support of Formula (IV) can have a grafted chain that includes a precursor group of the azlactone group. These precursor group can be subjected to a ring closure reaction to form the azlactone group. Once formed, the azlactone group can react as described above with various target compounds. The ring closure reaction can occur, for example, by treating the grafted support of Formula (IV) with acetic anhydride, trifluoroacetic anhydride, or alkyl chloroformates. This process is further described in U.S. Pat. No. 5,403,902 (Heilmann et al.) and U.S. Pat. No. 5,336,742 (Heilmann et al.).

In further embodiments of the grafted support of Formula (IV), the grafted chain has a glycidyl $Z^1$ group. The glycidyl group can undergo a ring-opening reaction with a target compound having a nucleophilic group. Suitable nucleophilic groups for reacting with a glycidyl group include, but are not limited to, primary amino groups, secondary amino groups, hydroxyl groups, tertiary amino groups, thiol groups, and carboxyl groups. The reaction of the glycidyl group with a nucleophilic group of the target compound usually results in the formation of a linkage group that functions to attach the target compound to the grafted chains. The linkage group formed by ring-opening of the glycidyl group often contains the group —C(OH)HCH$_2$—. The linkage group can be, for example, —C(OH)HCH$_2$NR$^3$— when the glycidyl group is reacted with an amino group, —C(OH)HCH$_2$O— when the glycidyl group is reacted with a hydroxyl group, —C(OH)HCH$_2$S— when the glycidyl group is reacted with a thiol group, or —C(OH)HCH$_2$O(CO)— when the glycidyl group is reacted with a carboxyl group.

In some applications, the grafted support of Formula (IV) can be further modified to provide other groups for interaction with or reaction with a target compound. In many embodiments, a modifying agent of formula A-T is reacted with the grafted support. In the formula A-T, group A is the modifying group and T is a remainder of the modifying agent and is equal to the modifying agent A-T minus the modifying group A. The modifying group A reacts with the functional group $Z^1$ on the grafted chains. The reaction of the functional group $Z^1$ and the modifying group A results in the formation of an attachment group L. The attachment group L is attached to T, which is the remainder of the modifying agent. The reaction is shown in Reaction Scheme C. $G\text{-}Z^1$ is used to refer to the grafted support of Formula (IV) that has a functional group $Z^1$ on the grafted chain.

$$G\text{-}Z^1 + A\text{-}T \longrightarrow G\text{-}L\text{-}T \qquad \text{Reaction Scheme C}$$

The formula $G\text{-}Z^1$ contains only one $Z^1$ group for ease of discussion. Many grafted supports have multiple grafted chains and many of the grafted chains have multiple $Z^1$ groups. Exemplary modifying agents are shown in Table 1 for each type of $Z^1$ functional group. In Table 1, the group X refers to a halo (e.g., $X^-$ is a halide) and group D is selected from oxy, thio, or $-NR^3-$. Each group $R^4$ is independently selected from hydrogen, alkyl, heteroalkyl, aryl, or aralkyl. Group $R^5$ is an alkylene. The group Az refers to an azlactone group and the group $Az^1$ refers to a ring-opened azlactone group.

TABLE 1

| Group G—$Z^1$ | Modifying Agent A—T | G—L—T |
|---|---|---|
| G—(CO)OH | HD—T | G—(CO)D—T |
| | (oxazoline structure with $R^4$, R) | G—(CO)O—C($R^4$)$_2$—C($R^4$)$_2$—NH(CO)—T |
| | (aziridine structure with $R^4$, N—T) | G—(CO)O—C($R^4$)$_2$—C($R^4$)$_2$—NH—T |
| | (epoxide-like structure with D, $R^4$, T) | G—(CO)O—C($R^4$)$_2$—C($R^4$)(DH)—T or G—(CO)O—C($R^4$)(T)—C($R^4$)$_2$(DH) |
| G—OH | O=C=N—T | G—(CO)—NH—T |
| | O=C=N—T | G—O(CO)—NH—T |
| | X—(CO)—T | G—O(CO)—T |
| | HO—(CO)—T | G—O(CO)—T |
| | (aziridine structure with $R^4$, N—T) | G—O—C($R^4$)$_2$—C($R^4$)$_2$—NH—T |
| | (epoxide-like structure with D, $R^4$, T) | G—O—C($R^4$)$_2$—C($R^4$)(DH)—T or G—O—C($R^4$)(T)—C($R^4$)$_2$(DH) |
| | (azlactone structure) | G—O(CO)—C($R^4$)2—NH—(CO)—T |
| | (anhydride structure) | G—O(CO)—T |
| G—N($R^3$)H | O=C=N—T | G—N($R^3$)(CO)—NH—T |
| | X—(CO)—T | G—N($R^3$)(CO)—T |
| | HO—(CO)—T | G—N($R^3$)(CO)—T |

TABLE 1-continued

Reaction of Grafted Support with Modifying Agent

| Group G—$Z^1$ | Modifying Agent A—T | G—L—T |
|---|---|---|
| | aziridine with $R^4$ groups, N—T | G—N($R^3$)—C($R^4$)$_2$—C($R^4$)$_2$—NH—T |
| | epoxide/cyclopropane with D, $R^4$, T | G—N($R^3$)—C($R^4$)$_2$—C($R^4$)(DH)(T) or G—N($R^3$)—C($R^4$)(T)—C($R^4$)$_2$(DH) |
| | azlactone with $R^4$, N, O, T | G—N($R^3$)(CO)—C($R^4$)2—NH—(CO)—T |
| | X—$R^5$—T | G—N$R^3$—$R^5$—T |
| | anhydride T—(CO)—O—(CO)—$R^4$ | G—N($R^3$)(CO)—T |
| G—N($R^3$)$_2$ <br> G—Az | X—$R^5$—T <br> HD—T | G—N$^+$($R^3$)$_2$—$R^5$—T X$^-$ <br> G—Az$^1$—D—T |
| 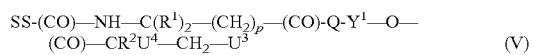 | HD—T | G—C(OH)$R^4$—C($R^4$)$_2$(D—T) or <br> G—C(D—T)$R^4$—C($R^4$)$_2$(OH) |
| | T—(CO)OH | G—C(OH)($R^4$)—C($R^4$)$_2$—OOC—T or <br> G—C($R^4$)(OOC—T)—C($R^4$)$_2$(OH) |

The modified solid support can be represented by Formula (V).

$$\text{SS-(CO)—NH—C($R^1$)}_2\text{—(CH}_2)_p\text{—(CO)-Q-Y}^1\text{—O—(CO)—CR}^2\text{U}^4\text{—CH}_2\text{—U}^3 \quad (V)$$

In Formula (V), SS is a solid support and $R^1$ is each independently selected from alkyl, heteroalkyl, aryl, or aralkyl. The group $R^2$ is hydrogen or an alkyl. The variable p is an integer equal to 0 or 1. Each group Q is independently a divalent group selected from oxy, thio, or —$NR^3$— where $R^3$ is hydrogen, alkyl, heteroalkyl, aryl, or aralkyl. The group $Y^1$ is a first linking group containing an alkylene, heteroalkylene, arylene, or combination thereof. $Y^1$ optionally can include an oxy, thio, amino, carbonylimino, carbonyloxy, carbonylthio, or a combination thereof separating one or more alkylenes, heteroalkylenes, arylenes, or mixtures thereof. The group $U^3$ includes at least one divalent monomeric unit of formula —$CR^2$($Y^2$-L-T)—$CH_2$—. Group $U^4$ is selected from hydrogen or a group that includes at least one divalent monomeric unit of formula —$CR^2$($Y^2$-L-T)—$CH_2$—. Group L is an attachment group formed by reacting a group $Z^1$ with a modifying group of a modifying agent of formula A-T where A is the modifying group. Group T is a remainder of the modifying agent A-T and is equal to the modifying agent A-T minus the modifying group A. Group $Z^1$ is a functional group selected from (1) an acidic group or a salt thereof, (2) an amino group or a salt thereof, (3) a hydroxyl group, (4) an azlactone group or a precursor of the azlactone group, (5) a glycidyl group, or (6) a combination thereof.

The modified grafted support can be used to separate and/or purify a target compound. That is, methods of separating or purifying a target compound are provided that include providing a grafted support of Formula (V) and contacting a sample containing the target compound with the grafted support. The target compound reacts with or interacts with the remainder group T of the modified grafted support. The modified grafted supports can function as affinity resins or materials, ion exchange resins or materials, hydrophobic interaction resins or materials, reverse phase resins or materials, size exclusion resins or materials, chelating resins or materials, cell selection resins or materials, immobilized enzyme resins or materials, mixed mode resins or materials, or the like.

Affinity resins or materials can be prepared, for example, by reacting a group $Z^1$ with a modifying agent that includes a modifying group plus an affinity ligand. An affinity ligand is a group or compound that can bind another group or compound. For example an azlactone group or a glycidyl $Z^1$ group on the grafted support of Formula (IV) can react with a modifying agent that contains a nucleophilic modifying group plus an affinity ligand. More particularly, an amino group of a biomolecule can react with the azlactone or glycidyl group to covalently attach the biomolecule to the grafted support. The attached biomolecule can interact with a complementary biomolecule. Exemplary modifying agents include an antigen that can bind to a corresponding (i.e., complementary) antibody or an antibody that can bind to a corresponding (i.e., complementary) antigen. Other exemplary modifying agents include a DNA or RNA fragment that can bind with a complementary DNA or RNA fragment and a lectin that can bind with a compound or biomolecule containing a carbohydrate moiety.

Ion exchange resins or materials can be prepared, for example, by reacting $Z^1$ on the grafted support of Formula (IV) with a modifying agent having a modifying group plus an ionic group. For example, the modifying agent can have a nucleophilic modifying group plus a second group that is basic, acidic, or a salt thereof. The nucleophilic group can react with an azlactone or glycidyl $Z^1$ group resulting in the attachment of an ionic group (i.e., acidic group, basic group, or salt thereof) to the grafted support. Suitable modifying agents having both a nucleophilic group and an ionic group include, but are not limited to, 2-aminoethylsulfonic acid or aminopropyldimethylamine.

Hydrophobic interaction resins or materials can be prepared, for example, by reacting a group $Z^1$ on the grafted support of Formula (IV) with a modifying agent having modifying group plus a hydrophobic group. For example, the modifying agent can have a nucleophilic modifying group that can react with an azlactone group or glycidyl $Z^1$ group resulting in the attachment of the hydrophobic group to the grafted support. Suitable modifying agents having both a nucleophilic group and a hydrophobic group include, but are not limited to, benzylamine, butylamine, hexylamine, or phenethylamine. Hydrophobic interaction resins can be used, for example, for purifying or separating relatively large molecules such as proteins.

Reverse phase resins or materials can be prepared, for example, using similar modifying agents to those used to prepare hydrophobic interaction resins. That is, reverse phase resins can be prepared by reacting an azlactone group or a glycidyl $Z^1$ group on a grafted support of Formula (IV) with a modifying agent having a nucleophilic modifying group and a second group that is hydrophobic. The nucleophilic group can react with the azlactone or the glycidyl $Z^1$ group resulting in the attachment of the modifying agent having a hydrophobic group to the grafted support. Suitable modifying agents having a nucleophilic group and a hydrophobic group include, for example, octyldecylamine. With reverse phase interaction resins, the eluent is usually an organic solvent rather than an aqueous-based solution. Further, reverse phase resins are typically used for the separation or purification of relatively small molecules and peptides rather than proteins.

Size exclusion resins or materials can be prepared, for example, by reacting a group $Z^1$ on the grafted support of Formula (IV) with a modifying agent having a modifying group and a second group that is non-interactive or neutral. For example, the modifying agent can include a nucleophilic modifying group that can react with an azlactone or glycidyl $Z^1$ group resulting in the attachment of the non-interactive or neutral group. Suitable modifying agents having both a nucleophilic group and a non-interactive or neutral group that can react with an azlactone $Z^1$ group include various amines, mercaptans, alcohols, or alcohol amines. For example, the modifying agent can be ethanolamine, ethanol, or ethylamine. Suitable modifying agents having both a nucleophilic group and a non-interactive or neutral group that can react with a glycidyl $Z^1$ group include various carboxylic acids and alcohols. For example, the modifying agent can be ethanol or acetic acid.

Chelating resins or materials can be prepared, for example, by reacting $Z^1$ on the grafted support Formula (IV) with a modifying agent having both a modifying group and a second group that is metal-chelating. For example, the modifying agent can have a nucleophilic modifying group that can react with an azlactone or glycidyl $Z^1$ group resulting in the attachment of the metal-chelating group. Suitable modifying agents include, but are not limited to, iminodiacetic acid, N-(3-aminopropyl)iminodiacetic acid, and N-(2-hydroxyethyl)iminodiacetic acid. The metal-chelating group, after chelation of a metal ion, can interact, for example, with certain groups on proteins such as histidine groups.

Cell selection resins can be prepared, for example, by reacting $Z^1$ on the grafted support of Formula (IV) with an antibody to a cell surface marker. That is, the antibody is the modifying agent. The antibody typically has a nucleophilic group such as an amino group that can react with an azlactone group or glycidyl group to attach the antibody to the grafted support. The antibody can in turn bind with a cell surface marker on the cell resulting in the attachment of the cell to the grafted support. Cell selection resins can be used, for example, to purify or separate stem cells, blood cells, or bacteria.

Immobilized enzyme resins can be prepared by reacting an azlactone or a glycidyl $Z^1$ group on the polymeric resin with a nucleophilic group of an enzyme to attach the enzyme to the grafted support. For example, the enzyme can be Penicillin G-acylase or glucoamylase. Immobilized enzyme resins can be used as catalysts for various reactions.

Mixed mode resins can be prepared by reacting a $Z^1$ group on the grafted support of Formula (IV) with modifying agents having a modifying group plus additional groups that can impart two or more interaction modes to the grafted support. The two or more modes of interaction can be any of those mentioned above. For example, an azlactone group or glycidyl group can be reacted with a modifying agent such as phenylalanine where the amino group would function as the nucleophilic group, the phenyl group would function as a hydrophobic group, and the carboxyl group would function as an ionic group.

In some embodiments, the grafted support or the modified grafted support is placed within a chromatographic column. The chromatographic column can be part of an analytical instrument or can be part of a preparative system. The preparative system can be of any suitable scale such as a laboratory scale, pilot plant scale, or industrial scale. In other embodiments, the grafted support or the modified grafted support can be disposed on a surface of a filtration medium. Any suitable filtration medium can be used. The filtration medium can be positioned within a cartridge to provide a filter cartridge. In many applications, the grafted supports or modified grafted supports are in the form of beads. The beads can have any suitable size.

EXAMPLES

These examples are merely for illustrative purposes and are not meant to be limiting on the scope of the appended claims. All parts, percentages, ratios, and the like in the examples and the rest of the specification are by weight, unless noted otherwise. Solvents and other reagents used were obtained from Sigma-Aldrich Chemical Company (Milwaukee, Wis.) unless otherwise noted.

Glossary Of Terms

| | |
|---|---|
| EMPHAZE AB1 | Polymeric beads commercially available from 3M Company (Saint Paul, MN) that are a reaction product of methylenebisacrylamide and 2-vinyl-4,4-dimethylazlactone. The beads contain about 5 weight percent azlactone. The average size is typically about 50 to 100 micrometers. |
| MBA | Methylenebisacrylamide |
| VDM | 2-vinyl-4,4-dimethylazlactone, available from SNPE, Inc, Princeton, NJ |
| HEMA | 2-Hydroxyethylmethacrylate |
| HEA | 2-Hydroxyethylacrylate |
| Polyethylene glycol 1000 | Polyethylene glycol having a weight average molecular weight of about 1000 g/mol |
| TMEDA | Tetramethylethylenediamine |
| DMSO | Dimethylsulfoxide |
| Triton X-100 | Nonionic surfactant |
| APTAC | Acrylamidopropyl trimethylammonium chloride |
| MAPTAC | (3-methacrylamidopropyl)trimethylammonium chloride |
| MOPS | 3-(N-morpholino)propanesulfonic acid |
| IgG | Human polyclonal Immunoglobulin G available from Equitech-Bio, Kerrville, TX |
| BSA | Bovine Serum Albumin |
| Protein A | Stock aqueous solution, approximately 50 mg/mL, available from Repligen Corporation, Waltham, MA |

Test Methods
Static Cation Exchange Capacity for Immunoglobulin G (IgG)

A 50 volume percent slurry of cation exchange polymeric beads was prepared by mixing the polymeric beads with deionized water, centrifuging at 3000 relative centrifugal force (rcf) for 20 minutes to form a packed bead bed, and then adjusting the amount of deionized water so that the total volume was twice that of the packed bead bed. The slurry was mixed well to suspend the polymeric beads, and then a 400 microliter sample of the slurry was pipetted into a 5 mL, 0.45 micrometer cellulose acetate centrifugal microfilter that is commercially available under the trade designation CENTREX MF through VWR (Eagan, Minn.). The water was removed by centrifugation at 3000 rcf for 5 minutes. The polymeric beads were then mixed with 4 mL of a buffer containing 50 mM sodium acetate and 80 mM sodium chloride at pH 4.5. The sample was centrifuged again at 3000 rcf for 10 minutes. The supernate was discarded. Then a 4.5 mL sample of IgG, having a concentration of about 7 mg/mL in the same acetate buffer was added to the filter containing the polymeric beads. The mixture was mixed by tumbling overnight, and then the supernate was removed from the polymeric beads by centrifugation at 3000 rcf for 20 min.

The supernate was analyzed by UV spectroscopy. The absorbance of the sample at 280 nm was compared to that of the starting IgG solution. The difference was used to calculate the IgG capacity of the polymeric beads. Assays were run in triplicate and averaged.

Cationic Dynamic Binding Capacity (DBC) for Immunoglobulin G (IgG)

An aqueous slurry of polymeric beads (approximately 350 microliter total volume of polymeric beads) was packed into a 5 centimeters by 0.3 centimeter inner diameter glass column commercially available under the trade designation OMNIFIT from Chromtech (Apple Valley, Minn.), placed on a Fast Protein Liquid Chromatograph commercially available under the trade designation AKTA from GE Healthcare (Uppsala, Sweden), and equilibrated for 10 column volumes with Buffer A (50 mM acetate, 40 mM NaCl) at 0.7 mL/minute. The pH of Buffer A was 4.5 unless otherwise noted otherwise. The challenge solution (5.0 mg/mL human IgG in buffer A) was loaded at 0.09 mL/min (3.9 minutes residence time/76 cm/hr) until 7 mL of sample was loaded or the UV absorbance at a wavelength of 280 nanometers ($A_{280}$) exceeded 800 mAU (whichever came first). The amount of IgG bound to the support was determined at the point where the concentration of the solution exiting the column during the initial loading was 10 percent of the initial IgG challenge solution concentration (the plateau of non-binding proteins was subtracted out).

Small Ion Capacity (SIC) for Hydrogen Ion

Approximately 8 mL of a polymeric bead slurry (approximately 50 volume percent in deionized water) was transferred to a 15 mL graduated centrifuge tube and centrifuged at 3000 relative centrifugal force (rcf) for 5 minutes. The volume of the resulting packed polymeric beads was recorded to the nearest 0.1 mL and the slurry was transferred quantitatively to a sintered glass funnel and washed with deionized water (3×50 mL), with 0.5N HCl (3×50 mL), and then again with deionized water (3×50 mL). The washed polymeric beads were then quantitatively transferred to a 125 mL Erlenmeyer flask and 4.0 mL of 2M NaCl was added to displace the hydrogen ions. After 5 minutes, 2 drops of phenolphthalein solution (1 gram in 100 mL ethanol) were added to the slurry and the mixture was titrated (while mixing on a magnetic stir plate) with 0.1 N NaOH until the solution was faint pink. The small ion capacity in micromoles per mL of polymeric beads was calculated by dividing the volume of 0.1 NaOH added by the volume of beads analyzed and multiplying by 100.

Static Anion Exchange Capacity for Bovine Serum Albumin (BSA)

A 50 volume percent slurry of anion exchange polymeric beads was prepared by mixing the polymeric beads with deionized water, centrifuging at 3000 relative centrifugal force (rcf) for 20 minutes to form a packed bead bed, and then adjusting the amount of deionized water so that the total volume was twice that of the packed bead bed. The slurry was mixed well to suspend the polymeric beads, and then a 400 microliter sample of the slurry was pipetted into a 5 mL, 0.45 micrometer cellulose acetate centrifugal microfilter that is commercially available under the trade designation CENTREX MF through VWR (Eagan, Minn.). The water was removed by centrifugation at 3000 rcf for 5 minutes. The polymeric beads were then mixed with 4 mL of a buffer containing 10 mM 3-(N-morpholino)propanesulfonic acid (MOPS) at pH 7.5. The sample was centrifuged again at 3000 rcf for 10 minutes. The supernate was discarded. Then a 4.5 mL sample of BSA, which was obtained from Sigma-Aldrich (St. Louis, Mo.), having a concentration of about 9 mg/mL in the same MOPS buffer was added to the filter containing the polymeric beads. The mixture was mixed by tumbling overnight, and then the supernate was removed from the polymeric beads by centrifugation at 3000 rcf for 20 min.

The supernate was analyzed by UV spectroscopy. The absorbance of the sample at 279 nm was compared to that of the starting BSA solution. The difference was used to calculate the BSA capacity of the polymeric beads. Assays were run in triplicate and averaged.

Anionic Dynamic Binding Capacity (DBC) for BSA

An aqueous slurry of polymeric beads (approximately 350 microliter total volume of polymeric beads) was packed into a 5 centimeters by 0.3 centimeter inner diameter glass column commercially available under the trade designation OMNIFIT from Chromtech (Apple Valley, Minn.), placed on a Fast Protein Liquid Chromatograph commercially available under the trade designation AKTA from GE Healthcare (Uppsala, Sweden), and equilibrated for 9 column volumes with Buffer A (25 mM tris(hydroxymethyl)aminomethane hydrochloride (Tris-HCl), pH 8.0) at 0.5 mL/minute. The challenge solution (5.0 mg/mL BSA in buffer A) was loaded at 0.1 mL/min (3.5 minutes residence time/85 cm/hr) until 15 mL of sample was loaded or the UV absorbance at a wavelength of 280 nanometers ($A_{280}$) exceeded 250 mAU (whichever came first). The amount of BSA bound to the support was determined at the point where the concentration of the solution exiting the column during the initial loading was 10 percent of the initial BSA challenge solution concentration.

Small Ion Capacity (SIC) for Hydroxide Ion

Approximately 8 mL of a polymeric bead slurry (approximately 50 volume percent in deionized water) was transferred to a 15 mL graduated centrifuge tube and centrifuged at 3000 relative centrifugal force (rcf) for 5 minutes. The volume of the resulting packed polymeric beads was recorded to the nearest 0.1 mL and the slurry was transferred quantitatively to a sintered glass funnel and washed with deionized water (3×50 mL), with 0.1N NaOH (3×50 mL), and then again with deionized water (3×50 mL). The washed polymeric beads were then quantitatively transferred to a 125 mL Erlenmeyer flask and 4.0 mL of 2M sodium sulfate was added to displace the hydroxide ions. After 5 minutes, 2 drops of phenolphthalein solution (1 gram in 100 mL ethanol) were added to the slurry and the mixture was titrated (while mixing on a magnetic stir plate) with 0.1 N HCl until the color of the solution changed from pink to colorless. The small ion capacity in micromoles per mL of polymeric beads was calculated by dividing the volume of 0.1HCl added by the volume of beads analyzed and multiplying by 100.

Static Affinity Binding Capacity for Immunoglobulin G (IgG)

A 50 volume percent slurry of Protein A derivatized polymeric beads was prepared by mixing the polymeric beads with deionized water, centrifuging at 3000 relative centrifugal force (rcf) for 20 minutes to form a packed bead bed, and then adjusting the amount of deionized water so that the total volume was twice that of the packed bead bed. The slurry was mixed well to suspend the polymeric beads, and then a 200 microliter sample of the slurry was pipetted into a 5 mL, 0.45 micrometer cellulose acetate centrifugal microfilter that is commercially available under the trade designation CENTREX MF through VWR (Eagan, Minn.). The water was removed by centrifugation at 3000 rcf for 5 minutes. The polymeric beads were then mixed with 2.25 mL of a human IgG solution (about 5 mg/mL hIgG, in 10 mM phosphate, 150 mM sodium chloride, pH 7.4). The mixture was mixed by tumbling overnight, and then the supernate was removed from the polymeric beads by centrifugation at 3000 rcf for 5 min.

The supernate was analyzed by UV spectroscopy. The absorbance of the sample at 280 nm was compared to that of the starting IgG solution. The difference was used to calculate the IgG capacity of the polymeric beads. Assays were run in triplicate and averaged.

Affinity Dynamic Binding Capacity (DBC) for Immunoglobulin G (IgG)

An aqueous slurry of Protein A derivatized polymeric beads (approximately 350 microliter total volume of polymeric beads) was packed into a 5 centimeters by 0.3 centimeter inner diameter glass column commercially available under the trade designation OMNIFIT from Chromtech (Apple Valley, Minn.), placed on a Fast Protein Liquid Chromatograph commercially available under the trade designation AKTA from GE Healthcare (Uppsala, Sweden), and equilibrated for 10 column volumes with Buffer A (10 mM phosphate, 150 mM sodium chloride, pH 7.4, spiked with 0.01% w/v sodium azide) at 0.7 mL/minute. The challenge solution (3.0 mg/mL human IgG in buffer A) was loaded at 0.09 mL/min (3.9 minutes residence time/76 cm/hr) until 7 mL of sample was loaded or the UV absorbance at a wavelength of 280 nanometers ($A_{280}$) exceeded 300 mAU (whichever came first). A washout of unbound sample was performed by flowing Buffer A at 0.7 mL/min flow rate for 18 column volumes. This was followed by isocratic elution with Buffer B (2% v/v glacial acetic acid, 0.1 M glycine) for 9 column volumes. The amount of IgG bound to the support was determined at the point where the concentration of the solution exiting the column during the initial loading was 10 percent of the initial IgG challenge solution concentration (the plateau of non-binding proteins was subtracted out). The column was then re-equilibrated by flowing 15 column volumes of Buffer A.

Example 1

A 15 gram sample of EMPHAZE AB1 beads was slurried in ethyl acetate (250 mL) in a 1 L round bottomed flask with overhead stirrer. 2-Hydroxyethylmethacrylate (HEMA, 15 mL) was added. After stirring for 5 minutes, borontrifluoride diethyletherate (300 μL) was added, and the mixture was allowed to react for 72 hours at ambient temperature. The bead slurry was then filtered, washed with acetone (4×250 mL), and dried overnight under vacuum.

Example 2

Example 1 was repeated except that 2-hydroxyethylacrylate (HEA) was used in place of HEMA.

Example 3

A 2 L split resin flask (Morton type) equipped with an overhead stirrer, heating control, reflux condenser, and nitrogen inlet was charged with toluene (188 mL) and polymeric stabilizer (0.13 g). The polymeric stabilizer was a 91.8: 8.2 by weight copolymer of isooctylacrylate and 2-acrylamidoisobutyramide that was prepared as described in Rasmussen, et al., *Makromol. Chem., Macromol. Symp.*, 54/55, 535-550 (1992). The solution was stirred at 450 rpm until all the stabilizer had dissolved. Heptane (348 mL) was added, and the mixture was heated under a slow nitrogen purge until the temperature equilibrated to 35° C. MBA (13.86 grams), and 2-acrylamido-2-methylalanine (0.14 gram) were weighed into a 225 mL Erlenmeyer flask. To the flask were added isopropanol (80 mL), deionized (DI) water (38.3 mL), 1N sodium hydroxide (1.78 mL), and polyethylene glycol 1000 (20 mL of a 50% w/w solution in DI water). The mixture was stirred at low heat until all monomers had dissolved. A solution of sodium persulfate (0.56 grams) in DI water (5 mL) was added with swirling to the monomer solution. The resulting solution was immediately added to the equilibrated reaction flask. Stirring and purging was continued until the batch had re-equilibrated to 35° C. Then tetramethylethylenediamine (TMEDA, 0.56 mL) was added to initiate polymerization. The polymerization reaction was allowed to proceed for a total of two hours. The bead suspension was filtered and washed with acetone (2×500 mL), methanol (2×500 mL), and again with acetone (2×500 mL). The wet filter cake was transferred to an Erlenmeyer flask, suspended in acetone (250 mL), and sonicated with swirling for 10 minutes to break up agglomerates. The beads were filtered, reslurried in water, and sieved using a RO-TAP sieve (W.S. Tyler, Mentor Ohio). The size fraction between 38-90 micrometers in diameter was collected. The mean particle size was determined to be 82.3 micrometers.

Approximately 20 mL of hydrated bead slurry was filtered and then washed with 0.1 N hydrochloric acid (2×50 mL), DI water (2×50 mL), acetone (3×50 ml), and dimethylsulfoxide (DMSO, 3×50 mL). The damp beads were placed in a 50 mL polypropylene centrifuge tube and diluted up to twice the swollen volume with DMSO. Acetic anhydride (1.7 mL) and triethylamine (0.1 mL) were added and the mixture was mixed for 4 hours at 25° C. The beads were filtered, washed with acetone (3×50 mL), and dried overnight under high vacuum. The dried beads were then reacted with HEMA as described in Example 1.

Example 4

Ethylenediamine (12.0 grams) was dissolved in isopropanol (200 mL), then a 20 gram sample of EMPHAZE AB 1 beads was added. The slurry was mixed for 2 hours at ambient temperature, filtered, and then washed with isopropanol (3×200 mL), distilled water (4×200 mL), 0.1 N HCl (3×200 ml), and distilled water (5×200 mL). The resultant amine-functional beads, when titrated by the procedure above for small ion exchange capacity for hydrogen ion, were determined to have an amine functionality of about 29 micromoles/mL of bead.

Half of the above slurry was filtered, washed with isopropanol (100 mL), isopropanol (100 mL) containing 0.1 N NaOH (20 mL) and isopropanol (3×100 mL). The wet cake was then slurried in isopropanol (about 50% by volume slurry), VDM (5 mL) was added, and the mixture was allowed to mix for 2 hours at ambient temperature. The beads were then filtered, washed with acetone (3×100 mL) and dried on a rotary evaporator at 60° C. for two hours to provide about 10 grams of acrylamide-functional beads, suitable for grafting reactions.

Example 5

Toluene (100 mL), heptane (300 mL), and Triton X-100 (1000 μL) were added to a 3-necked round bottomed flask. The mixture was purged with nitrogen while stirring with an overhead stirrer at room temperature.

In a separate 125 mL Erlenmeyer flask was dissolved AMPS (30 grams of a 50% w/w solution in water), sodium persulfate (0.20 grams), isopropanol (35 mL), and water (20 mL). HEMA-functionalized beads from Example 3 (2.0 grams) were added to the aqueous mixture and allowed to soak for 10 minutes. The beads were filtered to remove excess liquid and then transferred into the organic toluene/heptane mixture. The suspended beads were stirred and purged with nitrogen for 30 minutes before adding tetramethylethylenediamine (TMEDA, 0.2 mL). The mixture was stirred for 1 hour. The beads were filtered, washed with both acetone (3×100 mL) and DI water (3×100 mL), and then stored as a slurry in DI water for further analysis. The analysis of this material is shown in Table 1.

Examples 6 to 9

The procedure used to prepare Example 5 was repeated but with varying amounts of AMPS solution (10μ, 15, 20, and 40 grams, respectively). The amount of DI water was adjusted so that each reaction had a total of 35 mL of water. The analyses of these materials are shown in Table 1.

Examples 10 to 13

Examples 6 to 9 were repeated using the HEMA-functional beads of Preparative Example 1 along with 5, 10, 20, and 30 grams of AMPS solution, respectively. The analyses of these materials are shown in Table 1.

Examples 14 to 18

Example 12 was repeated, except that the amounts of isopropanol and water were varied. The amounts used were 0/70, 20/50, 49/21, and 60/10 mL, respectively, for Examples 14 to 17. For Example 18, 7.5 grams of AMPS solution, 7.5 mL isopropanol, and 18.75 mL DI water were used. The analyses of these materials are shown in Table 1.

Comparative Example 1

A 98:2 w/w MBA/AMA bead was prepared by a procedure similar to that of Example 3. This bead, without derivatization with HEMA, was subjected to the grafting procedure of Example 18. Small ion capacity of the resultant bead was 31 μmol/mL. This low small ion capacity indicates that very little, if any, grafting occurred.

TABLE 1

Characterization of Cation Exchange Beads

| Example | SIC (μmol/mL) | Static IgG (mg/mL) | DBC (pH 4.5) | DBC (pH 5.0) | DBC (pH 5.5) |
|---|---|---|---|---|---|
| 5 | 202 | 114 | 15.1 | 57.2 | 20.7 |
| 6 | 36 | 87 | 42.6 | 59.1 | 26.9 |
| 7 | 100 | 150 | 20.3 | 79.5 | 62.9 |
| 8 | 99 | 96 | 28.1 | 71.3 | 29.5 |
| 9 | 180 | 79 | 18.0 | 55.2 | 24.5 |
| 10 | 88 | 82 | 42.5 | | |
| 11 | 149 | 115 | 56.5 | | |
| 12 | 253 | 151 | 55.9 | | |
| 13 | 314 | 107 | 49.4 | | |
| 14 | 251 | 9 | 17.6 | | |
| 15 | 236 | 130 | 40.1 | | |
| 16 | 261 | 113 | 37.9 | | |
| 17 | 330 | 102 | 28.3 | | |
| 18 | 193 | 126 | 78.8 | | |

Example 19

The grafting procedure of Example 5 was repeated using HEMA-functional beads from Example 1 (2.0 grams), substituting APTAC (20 grams of a 75% solution by weight in water) for AMPS. The appropriate adjustment was made for the amount of added DI water due to the fact that the APTAC monomer is a 75% by weight solution in water rather than a 50% by weight solution in water. Characterization of the resultant grafted beads is shown in Table 2.

Examples 20-24

Example 19 was repeated, except that the amount of APTAC solution used was 15, 10, 7.5, 5, and 2.5 grams respectively. The amounts of added DI water were adjusted to provide a total of 17.5 mL water. Characterization of the resultant grafted beads is shown in Table 2.

Examples 25-29

Example 19 was repeated, using HEMA-functional beads from Example 1 (1 gram), and substituting varying amounts of (3-methacrylamidopropyl)trimethylammonium chloride (MAPTAC, 50% solution by weight in water) for APTAC. Again, adjustment were made to the amounts of DI water added to provide a total of 17.5 mL water. Amounts of MAP- TAC solution used were 20, 15, 10, 7.5, and 5 grams, respectively. Characterization of the resultant grafted beads is shown in Table 2.

TABLE 2

Grafted Anion Exchange Beads

| Example | SIC (μmol/mL) | Static BSA (mg/mL) | DBC (pH 8.0) |
|---|---|---|---|
| 19 | 442 | 75.3 | 45.9 |
| 20 | 382 | 99.7 | 69.2 |
| 21 | 300 | 143.5 | 92.6 |
| 22 | 188 | 169.0 | 89.2 |
| 23 | 123 | 161.9 | 74.7 |
| 24 | 55 | 89.4 | 50.0 |
| 25 | 260 | 144.3 | 81.2 |
| 26 | 192 | 132.2 | 95.5 |
| 27 | 161 | 138.2 | 82.6 |
| 28 | 133 | 137.0 | 82.2 |
| 29 | 95 | 116.5 | 49.6 |

Example 30

Toluene (50 mL), heptane (150 mL), and Triton X-100 (500 μL) were added to a 3-necked round bottomed flask. The mixture was purged with nitrogen while stirring with an overhead stirrer at room temperature.

N-acryloyl-2-methylalanine (AMA, 30 milligrams), methacrylamide (MA, 544 milligrams), sodium persulfate (0.12 grams), isopropanol (17.5 mL), 0.1 N sodium hydroxide (1.92 mL), and deionized water (15.58 mL) were dissolved in a separate 125 mL Erlenmeyer flask. HEMA-functionalized beads from Example 3 (1.0 gram) were added to the aqueous mixture and allowed to soak for 10 minutes. The beads were filtered to remove excess liquid, and then transferred into the organic toluene/heptane mixture. The suspended beads were stirred and purged with nitrogen for 30 minutes before adding tetramethylethylenediamine (TMEDA, 0.1 mL). The mixture was stirred for 1 hour and then the beads were filtered. The filtered beads were washed with acetone (3×50 mL), DI water (3×50 mL), 0.1 N hydrochloric acid (2×50 mL), DI water (2×50 mL), acetone (3×50 ml), and then dimethylsulfoxide (DMSO, 3×50 mL). The damp beads were placed in a 50 mL polypropylene centrifuge tube and diluted up to 2× the swollen volume with DMSO. Acetic anhydride (1.7 mL) and triethylamine (0.1 mL) were added and the mixture was mixed for 4 hours at 25° C. The beads were filtered, washed with acetone (3×50 mL), and dried overnight under high vacuum. Infrared analysis indicated successful cyclization to the azlactone by the presence of an absorption band at ca. 1820 cm$^{-1}$.

Example 31

A Protein A coupling solution was prepared by combining 1.87 mL of Buffer "A" (0.135 M MOPS, 1.018 M sodium sulfate, pH 7.55), 0.4 mL deionized water, and 0.532 mL Protein A stock solution (50 mg/mL). This solution and a separate solution, 5.0 mL of Buffer "B" (0.100 M MOPS, 0.4 M TRIS, 1.27 M sodium sulfate, pH 7.5), were equilibrated by means of a water bath to 25° C. To a 15 mL polypropylene centrifuge tube was added 200 mg of the dry azlactone-functional beads from Example 26, followed by 2.80 mL of the Protein A coupling solution. The resultant slurry was mixed on an orbital shaker for 15 minutes. Buffer "B" was added and mixing was continued for an additional hour at 25° C. The bead slurry was centrifuged at 3000 rcf for 5 minutes, the supernate was decanted, and ethanolamine quench buffer (5 mL, 3.0 M ethanolamine, pH 9.0) was added. This mixture was mixed for 1 hour at ambient temperature, filtered, and washed with pH 7.5 phosphate buffer (5×20 mL), then stored as a 20% ethanol solution (vol/vol) in water at 10° C. The static affinity binding capacity for IgG was measured as 55 mg/mL, while the dynamic binding capacity at 10% breakthrough was determined to be 35 mg/mL.

Example 32

Toluene (50 mL), heptane (150 mL), and Triton X-100 (500 μL) was added to a 3-necked round bottomed flask. The mixture was purged with nitrogen while stirring with an overhead stirrer at room temperature.

N-acryloyl-2-methylalanine, sodium salt (AMA-Na, 1.0 grams of a 40% solids by weight in water), sodium persulfate (0.12 grams), isopropanol (17.5 mL), and deionized water (16.9 mL) were dissolved in a separate 125 mL Erlenmeyer flask. HEMA-functionalized beads from Example 1 (1.0 gram) were added to the aqueous mixture and allowed to soak for 20 minutes. The beads were filtered to remove excess liquid, and then transferred into the organic toluene/heptane mixture. The suspended beads were stirred and purged with nitrogen for 60 minutes before adding tetramethylethylenediamine (TMEDA, 0.1 mL). The mixture was stirred for 2 hours, the beads were filtered, washed with acetone (3×50 mL), DI water (3×50 mL), 0.1 N hydrochloric acid (2×50 mL), DI water (2×50 mL), acetone (3×50 ml), and then dimethylsulfoxide (DMSO, 3×50 mL). The damp beads were placed in a 50 mL polypropylene centrifuge tube and diluted up to 2× the swollen volume with DMSO. Acetic anhydride (1.7 mL) and triethylamine (0.1 mL) were added and the mixture was mixed for 4 hours at 25° C. The beads were filtered, washed with acetone (3×50 mL), and dried overnight under high vacuum. Quantitative analysis of the infrared absorption band at ca. 1820 cm$^{-1}$ indicated an azlactone content of 9.5% by weight.

Examples 33-34

Example 32 was repeated, utilizing 2.5 grams and 20 grams, respectively, of AMA-Na solution, with adjustment of the amount of added deionized water to 16 mL and 5.5 mL respectively. Infrared analysis of the resultant grafted beads indicated azlactone contents of 14.2% and 27.2% by weight, respectively.

We claim:

1. An article comprising a (meth)acryloyl-functionalized support of Formula (II)

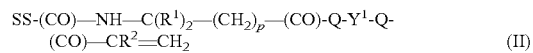
(II)

wherein
SS is a solid support;
p is an integer equal to 0 or 1;
each $R^1$ is independently selected from alkyl, heteroalkyl, aryl, or aralkyl;
each Q is independently a divalent group selected from oxy, thio, or —$NR^3$— where $R^3$ is hydrogen, alkyl, heteroalkyl, aryl, or aralkyl;
$Y^1$ is a first linking group that comprises an alkylene, heteroalkylene, arylene, or combination thereof; and
each $R^2$ is independently hydrogen or an alkyl.

2. The article of claim 1, wherein the solid support is in the form of a bead.

3. The article of claim 1, wherein the solid support comprises a crosslinked polymeric material.

4. The article of claim 1, wherein the solid support is in the form of a membrane, foam, film, sheet, or coating on a substrate.

5. The article of claim 1, wherein each Q is oxy.

6. The article of claim 1, wherein $Y^1$ is an alkylene.

7. An article comprising a grafted support of Formula (IV)

$$\text{SS-(CO)—NH—C}(R^1)_2\text{—(CH}_2)_p\text{—(CO)-Q-}Y^1\text{-Q-(CO)—CR}^2U^2\text{—CH}_2\text{—U}^1 \quad (IV)$$

wherein
- SS comprises a solid support in the form of a membrane, foam, film, sheet, or coating on a substrate;
- p is an integer equal to 0 or 1;
- each $R^1$ is each independently selected from alkyl, heteroalkyl, aryl, or aralkyl;
- each Q is independently a divalent group selected from oxy, thio, or —$NR^3$— where $R^3$ is hydrogen, alkyl, heteroalkyl, aryl, or aralkyl;
- $Y^1$ is a first linking group that comprises an alkylene, heteroalkylene, arylene, or combination thereof;
- each $R^2$ is independently hydrogen or an alkyl;
- $U^1$ comprises at least one divalent monomeric unit of formula —$CR^2(Y^2Z^1)$—$CH_2$—;
- $U^2$ is hydrogen or comprises at least one divalent monomeric unit of formula —$CR^2(Y^2Z^1)$—$CH_2$—;
- $Y^2$ is a second linking group selected from a single bond or a divalent group comprising an alkylene, heteroalkylene, arylene, or combination thereof; and
- $Z^1$ is a functional group selected from (1) an acidic group or a salt thereof, (2) an amino group or a salt thereof, (3) a hydroxyl group, (4) an azlactone group or a precursor of the azlactone group, (5) a glycidyl group, or (6) a combination thereof.

8. The article of claim 7, wherein each Q is oxy.

9. The article of claim 7, wherein $Y^1$ is an alkylene.

* * * * *

UNITED STATES PATENT AND TRADEMARK OFFICE
CERTIFICATE OF CORRECTION

PATENT NO. : 9,018,267 B2
APPLICATION NO. : 14/254247
DATED : April 28, 2015
INVENTOR(S) : Simon Shannon Page 1 of 2

It is certified that error appears in the above-identified patent and that said Letters Patent is hereby corrected as shown below:

Title Page

Page 2, Column 2 (Other Publications)
Line 10, delete "AB 1'"" and insert -- AB1" --, therefor.

Specification

Column 2
Line 24 (Approx.), delete "U'" and insert -- $U^1$ --, therefor.

Line 36 (Approx.), delete "$C(R^1)_2$," and insert -- $C(R^1)_2$ --, therefor.

Column 8
Line 24, delete "et al.)" and insert -- et al.). --, therefor.

Column 11
Line 15, delete "a a" and insert -- a --, therefor.

Column 13
Line 22, delete "$AZ^1$"" and insert -- $A_Z^1$ --, therefor.

Line 22, delete "$Y^{1a}Q$" and insert -- $Y^{1a}$—Q --, therefor.

Line 62, delete "(meth)acrylolyl" and insert -- (meth)acryloyl --, therefor.

Line 64 (Approx.), delete "$Y^{2a}Q$" and insert -- $Y^{2a}$—Q --, therefor.

Column 14
Line 57, after "Q," delete "y".

Signed and Sealed this
Fifth Day of January, 2016

Michelle K. Lee
*Director of the United States Patent and Trademark Office*

CERTIFICATE OF CORRECTION (continued)
U.S. Pat. No. 9,018,267 B2

Specification

Column 15
Line 54, delete "Z'" and insert -- $Z^1$ --, therefor.

Columns 19-20
Line 5 (Approx.) (Table 1), delete " 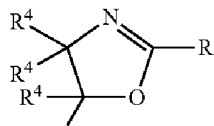 " and insert -- 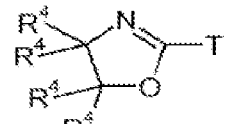 --, therefor.

Column 21
Line 45, delete "—O—" and insert -- —Q— --, therefor.

Column 29
Line 14, delete "AB 1" and insert -- AB1 --, therefor.

Claims

Column 33
Line 15, in Claim 7, after "is" delete "each".